United States Patent [19]
Asaka et al.

[11] Patent Number: 5,631,354
[45] Date of Patent: May 20, 1997

[54] 5-O-DESOSAMINYLERYTHRONOLIDE DERIVATIVES

[75] Inventors: Toshifumi Asaka; Yoko Misawa; Masato Kashimura; Shigeo Morimoto; Katsuo Hatayama, all of Tokyo, Japan

[73] Assignee: Taisho Pharmaceutical Co., Ltd., Japan

[21] Appl. No.: 256,124

[22] PCT Filed: Dec. 25, 1992

[86] PCT No.: PCT/JP92/01714

§ 371 Date: Jun. 21, 1994

§ 102(e) Date: Jun. 21, 1994

[87] PCT Pub. No.: WO93/13116

PCT Pub. Date: Jul. 8, 1993

[30] Foreign Application Priority Data

| Dec. 27, 1991 | [JP] | Japan | 3-346826 |
| Jul. 27, 1992 | [JP] | Japan | 4-199368 |
| Oct. 19, 1992 | [JP] | Japan | 4-279867 |

[51] Int. Cl.$^6$ .................................................. C07H 17/08
[52] U.S. Cl. .................................................. 536/7.4; 536/7.2
[58] Field of Search .................................................. 536/7.2, 7.4

[56] References Cited

U.S. PATENT DOCUMENTS

| 3,923,784 | 12/1975 | Kierstead et al. | 536/7.2 |
| 4,518,590 | 5/1985 | Hauske et al. | 514/29 |
| 4,742,049 | 5/1988 | Baker et al. | 514/29 |
| 4,921,839 | 5/1990 | Brain et al. | 514/29 |

FOREIGN PATENT DOCUMENTS 0216169  1/1987  European Pat. Off. .

OTHER PUBLICATIONS

Journal of Medicinal Chemistry, 1975, vol. 18 No. 8, pp. 849–851.

*Primary Examiner*—Elli Peselev
*Attorney, Agent, or Firm*—Lorusso & Loud

[57] ABSTRACT

Object:

Provision of novel macrolide antibiotics having a strong antibacterial activity.

Construction:

Compounds represented by the formula:

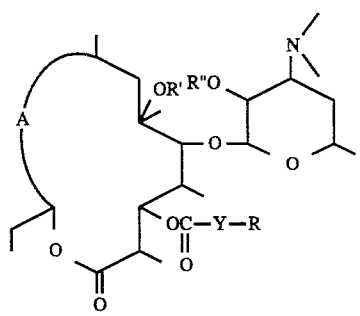

which are obtained by introducing a certain substituted carbonyloxy group into 5-O-desosaminylerythronolide derivatives at the 3-position; and pharmaceutically acceptable acid addition salts thereof.

13 Claims, No Drawings

5-O-DESOSAMINYLERYTHRONOLIDE DERIVATIVES

TECHNICAL FIELD

The present invention relates to novel derivatives of an antibiotic erythromycin. More particularly, it relates to novel derivatives of 5-O-desosaminylerythronolide derivatives and pharmaceutically acceptable acid addition salts thereof.

BACKGROUND ART

Erythromycin is an antibiotic clinically widely used as an agent for curing infectious diseases caused by Gram-positive bacteria, some Gram-negative bacteria, mycoplasmas, etc. Many derivatives of erythromycin have been produced for improving the biological and/or pharmacodynamic characteristics of erythromycin. As 5-O-desosaminylerythronolide derivatives, 3-O-acyl-5-O-desosaminylerythronolide derivatives, for example, have been disclosed in U.S. Pat. No. 3,923,784. 5-O-desosaminylerythronolide derivatives, however, have been generally considered to be poor in antibacterial activity, and the antibacterial activity of the above-exemplified derivatives is also very weak. An object of the present invention is to provide novel antibiotics having a strong antibacterial activity.

DISCLOSURE OF THE INVENTION

The present inventors conducted various researches on the antibacterial activity of 5-O-desosaminylerythronolide derivatives and consequently found that compounds obtained by introducing a certain substituted carbonyloxy group into 5-O-desosaminylerythronolide derivatives at the 3-position have a very strong antibacterial activity unexpectedly, whereby the present invention has been accomplished.

The present invention is 5-O-desosaminylerythronolide derivatives represented by the formula:

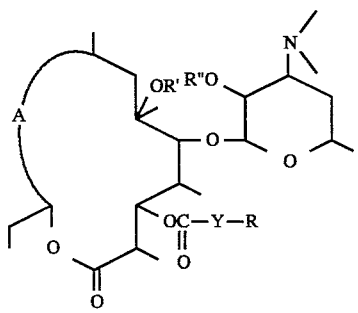

[wherein Y is a group represented by the formula:

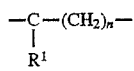

(wherein $R^1$ is a hydrogen atom, a hydroxyl group, a halogen atom, a $C_1$–$C_3$ alkyl group, a $C_1$–$C_{10}$ alkylamino group, a $C_7$–$C_{15}$ aralkylamino group, an amino group, a $C_2$–$C_{10}$ acylamino group, or a $C_2$–$C_{10}$ acylamino group containing at least one nitrogen atom or oxygen atom, and n is an integer of 0 to 4), an oxygen atom, a vinylene group, or a group represented by the formula —$CH_2$—NH—CO—, R is a hydrogen atom; a $C_1$–$C_5$ alkyl group; a $C_1$–$C_5$ alkyl group containing at least one nitrogen atom, oxygen atom or sulfur atom; a $C_7$–$C_{15}$ aralkyl group; a $C_7$–$C_{15}$ aralkyl group containing at least one nitrogen atom, oxygen atom or sulfur atom; a phenyl group; a substituted phenyl group having 1 to 5 substituents selected from halogen atoms, nitro groups, amino groups, $C_1$–$C_3$ alkyl groups, substituted $C_1$–$C_3$ alkyl groups having one or more halogen atoms as the substituent (s), $C_1$–$C_4$ alkylamino groups, $C_2$–$C_7$ acylamino groups and $C_1$–$C_4$ alkoxy groups; a naphthyl group; a thiazolyl group; an imidazolyl group; an aminothiazolyl group; a biphenyl group; a thienyl group; a pyridyl group; a substituted pyridyl group having one or more nitro groups as the substituent(s); a phenylthio group; a substituted phenyloxy group having one or more halogen atoms or nitro groups as the substituent (s); or an indolyl group (but in the case of Y being an oxygen atom, R is not a hydrogen atom), A is a group represented by the formula (i):

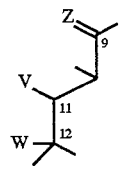

(wherein Z is an oxygen atom or a group represented by the formula =N—O—$R^4$ (wherein $R^4$ is a hydrogen atom; a $C_1$–$C_8$ alkyl group; a $C_2$–$C_{18}$ alkyl group containing at least one nitrogen atom, oxygen atom or sulfur atom; a benzyl group; or a substituted benzyl group having 1 to 5 substituents selected from halogen atoms and $C_1$–$C_4$ alkyl groups), V is a hydroxyl group and W is a hydrogen atom or a hydroxyl group, or V and W represent together with the carbon atoms at the 11- and 12-positions a group represented by the formula:

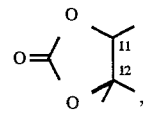

or a group represented by the formula:

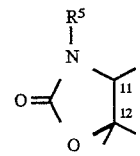

(wherein $R^5$ is a hydrogen atom or a $C_1$–$C_3$ alkyl group), a group represented by the formula (ii):

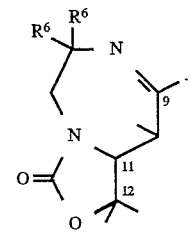

(wherein $R^6$ is a hydrogen atom or a $C_1$–$C_3$ alkyl group), or a group represented by the formula (iii):

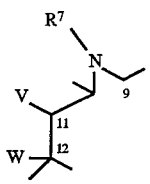

(wherein $R^7$ is a hydrogen atom, a $C_1$-$C_4$ alkyl group, a $C_3$-$C_5$ alkenyl group or a $C_3$-$C_5$ alkynyl group, and V and W are as defined above), R' is a hydrogen atom, a $C_1$-$C_5$ alkyl group, a carbamoyl group or an acetyl group, R" is a hydrogen atom, a $C_2$-$C_{15}$ alkoxycarbonyl group, a $C_2$-$C_{15}$ alkoxycarbonyl group containing at least one oxygen atom in its alkyl moiety, a $C_2$-$C_{15}$ acyl group, a $C_2$-$C_{15}$ acyl group containing at least one oxygen atom, or a pyridylcarbonyl group] and pharmaceutically acceptable acid addition salts thereof.

In the present invention, the halogen atoms are fluorine, chlorine, bromine and iodine atoms. The term "alkyl group" means a linear or branched alkyl group. The term "alkylamino group" means a substituted amino group having one or two linear or branched alkyl groups as the substituent(s), and there can be exemplified methylamino group, dimethylamino group, diethylamino group, dipropylamino group, diisopropylamino group, hexylamino group and heptylamino group. The term "aralkylamino group" means a substituted amino group having one or two aralkyl groups as the substituent(s), and there can be exemplified benzylamino group, dibenzylamino group and N-methyl-N-benzylamino group.

The term "acylamino group" means a substituted amino group having an aliphatic or aromatic acyl group as the substituent, and there can be exemplified acetyl amino group, propionylamino group, butyrylamino group and benzoylamino group.

The term "$C_2$-$C_{10}$ acylamino group containing at least one nitrogen atom or oxygen atom" means a substituted amino group having an aliphatic or aromatic acyl group as the substituent as follows: when the substituent is an aliphatic acyl group, its chain portions are linked to each other through NH or O, or the hydrogen atom of the aliphatic is replaced by a nitro group, an amino group, an alkylamino group, a hydroxyl group or an alkoxy group; when the substituent is aromatic, the hydrogen atom on the ring is replaced by a nitro group, amino group, alkylamino group, hydroxyl group or alkoxy group. As such acylamino groups, there can be exemplified
—$NHCOCH_2CH_2NHCH_3$,
—$NHCOCH_2CH_2NHCH_2CH_3$,
—$NHCOCH_2CH_2NHCH(CH_3)_2$,
—$NHCOCH_2CH_2OCH_2CH_3$,
—$NHCOCH_2CH_2OCH_3$,
—$NHCOCH_2CH_2OCH_2CH_2OCH_2CH_2OCH_2CH_3$,
—$NHCOCH_2CH_2NO_2$,
—$NHCOCH_2CH_2CH(NHCH_3)CH_3$,
—$NHCOCH_2CH_2CH(OH)CH_3$,
—$NHCOCH_2CH(OCH_3)CH_2CH_3$,
—NH-prolyl,
—$NHCOCH(NH_2)C_6H_5$,
—$NHCOCH(NH_2)CH_2C_6H_4(OH$-p$)$,
—$NHCOC_6H_5$,
—$COC_6H_4(NH_2$-p$)$,
—$NHCOC_6H_4(NO_2$-p$)$,
—$NHCOC_6H_4(NHCH_3$-p$)$,
—$NHCOC_6H_4(OH$-p$)$,
—$NHCOC_6H_4(OCH_3$-o$)$.

As the $C_1$-$C_{15}$ alkyl group containing at least one nitrogen atom, oxygen atom or sulfur atom, there can be exemplified
—$CH_2CH_2OCH_3$,
—$CH_2CH_2OCH_2CH_2OCH_3$,
—$CH_2CH_2OCH_2CH_2OCH_2CH_2OCH_3$,
—$CH_2CH_2OCH_2CH_2OCH_2CH_2OCH_2CH_2OCH_3$,
—$CH_2CH_2CH_2OCH_3$,
—$CH_2CH_2SCH_3$,
—$CH_2CH_2(NH)CH_2CH_2N(CH_3)_2$.

As the aralkyl group, there can be exemplified benzyl group, diphenylmethyl group, triphenylmethyl group and anthracenylmethyl group.

As the aralkyl group containing at least one nitrogen atom, oxygen atom or sulfur atom, there can be exemplified nitrobenzyl group, methoxybenzyl group, methylthiobenzyl group, methoxycarbonylbenzyl group, carboxybenzyl group and methylenedioxybenzyl group.

As the substituted $C_1$-$C_3$ alkyl groups having one or more halogen atoms as the substituent(s), there can be exemplified trifluoromethyl group, ditrifluoromethyl group, fluoromethyl group and trichloromethyl group.

As the $C_1$-$C_4$ alkoxy groups, there can be exemplified methoxy group, ethoxy group, t-butoxy group, isopropoxy group and methoxyethoxy group.

As the $C_3$-$C_5$ alkenyl group, there can be exemplified allyl group and prenyl group.

As the $C_3$-$C_5$ alkynyl group, there can be exemplified propargyl group and 3-methylpropargyl.

The term "$C_2$-$C_{15}$ alkoxycarbonyl group" means a substituted carbonyl group having an alkoxy group as the substituent, and there can be exemplified methoxycarbonyl group and benzyloxycarbonyl group.

As the $C_2$-$C_{15}$ alkoxycarbonyl group containing at least one oxygen atom in its alkyl moiety, there can be exemplified 2-methoxyethoxycarbonyl group, 2-[2-(2-methoxyethoxy)ethoxy]ethoxycarbonyl group and 2-[2-(2ethoxyethoxy)ethoxy]ethoxycarbonyl group.

As the $C_2$-$C_{15}$ acyl group, there can be exemplified acetyl group, propionyl group and benzoyl group.

The term "$C_2$-$C_{15}$ acyl group containing at least one oxygen atom in its alkyl moiety" means a substituted acyl group having an alkoxycarbonyl group as the substituent, and ethylsuccinyl group can be exemplified.

As the pharmaceutically acceptable acid addition salts, there can be exemplified acetates, propionates, butyrates, formates, trifluoroacetates, maleates, tartarates, citrates, stearates, succinates, ethylsuccinates, lactobionates, gluconates, glucoheptonates, benzoates, methanesulfonates, ethanesulfonates, 2-hydroxyethanesulfonates, benzenesulfonates, p-toluenesulfonates, laurylsulfates, malates, aspartates, glutaminates, adipates, cysteine salts, hydrochlorides, hydrobromides, phosphates, sulfates, hydroiodides, nicotinates, oxalates, picrates, thiocyanates, undecanoates, polyacrylates and carboxyvinyl polymer salts.

The compounds of the present invention include both those in which the coordination at the 3-position is natural (3S forms) and those in which the coordination at the 3-position is not natural (3R forms).

The compounds of the present invention can be produced, for example, as follows. But, a process for producing the compound of the present invention is not limited to the processes described below.

[Production process 1]

Process using 5-O-desosaminyl-6-O-methylerythronolide A as a starting material

Step (1):

5-O-desosaminyl-6-O-methylerythronolide A is reacted with an acid anhydride of the formula R''₂O (wherein R'' is an alkoxy group or a benzoyl group) or a halide of the formula R''—X (wherein R'' is as defined above, and X is an optional halogen atom) and a base in an inert solvent at 0° C. to 30° C., whereby there can be obtained a compound of the formula (a):

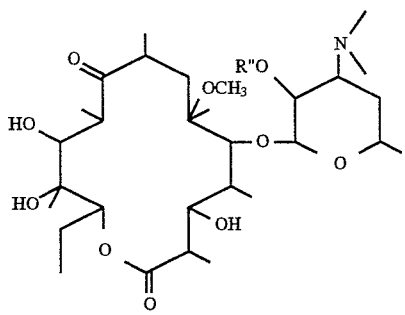
(a)

wherein R'' is as defined above. Here, as the suitable inert solvent, there are used dichloromethane, dichloroethane, acetone, pyridine, ethyl acetate, tetrahydrofuran, etc. As the acid anhydride or the halide, there are used anhydrides and halides of acetic acid, propionic acid, benzoic acid and pyridinecarboxylic acid, and carbonate ester halides such as 2-[2-(2-methoxyethoxy)ethoxy]ethyl chloroformate. As the base, there are used sodium hydrogencarbonate, sodium carbonate, potassium carbonate, triethylamine, pyridine, tributylamine, etc.

Step (2):

The compound obtained in step (1) is reacted with an acid anhydride of the formula (Y'—CO)₂O [wherein Y' is a group of the formula:

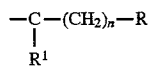

(wherein R, R¹ and n are as defined above) or a group of the formula —CH=CH—R (wherein R is as defined above)], an acid halide of the formula Y'—CO—X (wherein Y' and X are as defined above), a mixed acid anhydride of the formula Y'—COO—R⁶ (wherein Y' is as defined above, and R⁸ is a group usually used for preparing a mixed acid anhydride, such as pivaloyl group, p-toluenesulfonyl group, isobutoxycarbonyl group, ethoxycarbonyl group or isopropoxycarbonyl group), a carboxylic acid of the formula Y'—COOH (wherein Y' is as defined above) and dicyclohexylcarbodiimide or 1-ethyl-3-(3-dimethylaminopropyl)carbodiimide hydrochloride and by use of a base in an inert solvent at −20° to 60° C., preferably −20° C. to room temperature, whereby there can be obtained a compound of the present invention of the formula (b):

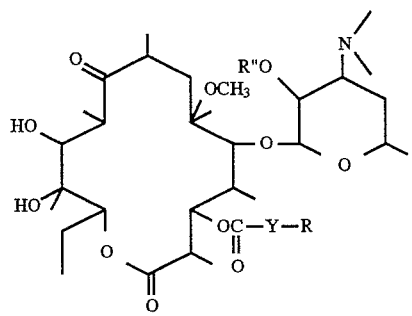
(b)

wherein R, R'' and Y are as defined above.

The compound of the present invention of the formula (b) can be obtained also by reacting the compound obtained in step (1) with a chloroformate of the formula R⁹—O—CO—Cl (wherein R⁹ is a group selected from the following groups for R: the C₂–C₁₅ alkyl groups containing at least one nitrogen atom, oxygen atom or sulfur atom, the C₁–C₁₅ alkyl groups, the aralkyl groups containing at least one nitrogen atom, oxygen atom or sulfur atom, and the aralkyl groups) and a base in an inert solvent at 0° C. to 30° C. Here, the suitable inert solvent is the same as used in step (1). As the base, there are used pyridine, collidine, N-methylpiperidine, N-methylmorpholine, triethylamine, 4-dimethylaminopyridine, etc.

Step (3):

The compound obtained in step (2) is reacted in a lower alcohol at room temperature to 100° C., whereby there can be obtained a compound of the present invention of the formula (c):

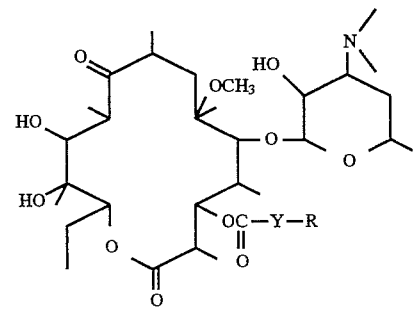
(c)

wherein R and Y are as defined above. Here, as the lower alcohol, there are used methanol, ethanol, propanol, butanol, etc.

Step (4):

The compound obtained in step (2) is with a reagent such as phosgene dimer or phosgene trimer under ice-cooling in a suitable inert solvent by use of a base such as pyridine, whereby there can be obtained a compound of the formula (d):

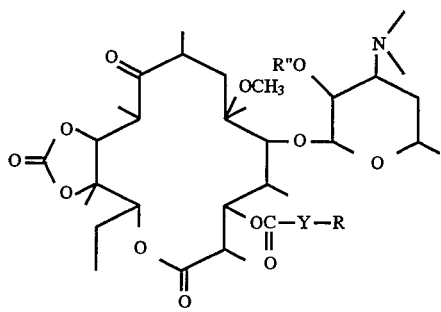

(d)

wherein R, R" and Y are as defined above. Here, the suitable inert solvent is the same as used in step (1).

Step (5):

The compound of the formula (d) can be produced also by reacting the compound obtained in step (1), in the same manner as in step (4), thereafter placing an alcohol of the formula $R^2$—OH (wherein $R^2$ is as defined above) in the same reactor, and then carrying out the reaction at 0° C. to room temperature. Then, the compound (d) is reacted in the same manner as in step (3), whereby there can be produced a compound of the present invention of the formula (e):

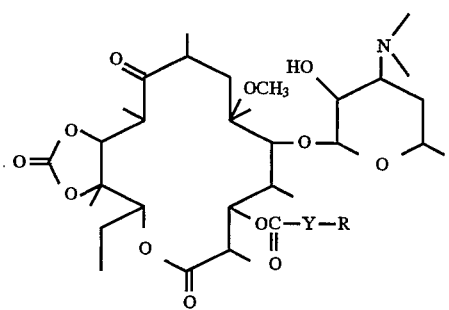

(e)

wherein R and Y are as defined above.

Step (6):

For producing a tricyclic carbamate represented by combination with the carbon atoms at the 9- to 12-positions, the compound obtained in step (1) is reacted with phosgene dimer or phosgene trimer in the same manner as in step (4), after which excess benzyl alcohol was added to obtain a compound of the formula (f):

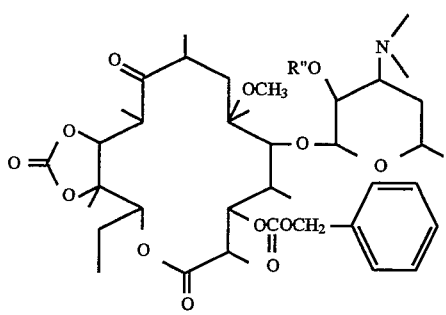

(f)

wherein R" is as defined above. Then, this compound is reacted with 1,1'-carbonyldiimidazole and a base in a suitable solvent at room temperature, whereby there can be obtained a compound of the formula (g):

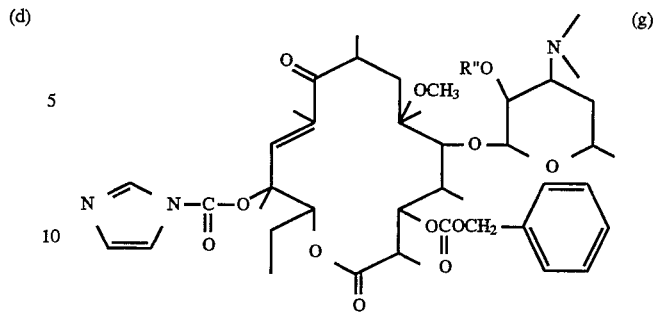

(g)

wherein R" is as defined above. Here, as a suitable solvent, there are used dimethylformamide, N-methylpyrrolidone, tetrahydrofuran, acetonitrile, mixed solvents thereof, etc. As the base, there are used sodium hydride, potassium hydroxide, sodium bistrimethylsilylamide, etc.

Step (7):

The compound obtained in step (6) is reacted by addition of a reagent of the formula:

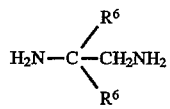

(wherein $R^6$ is as defined above) in an inert solvent at room temperature to obtain a compound of the formula (h):

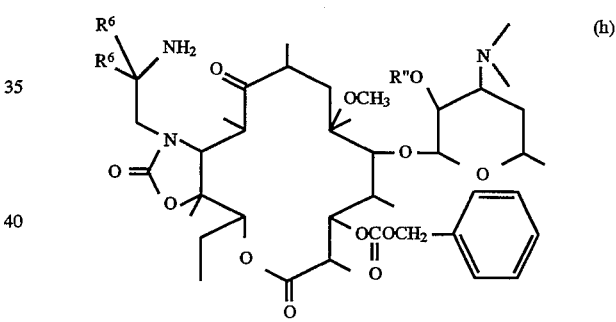

(h)

(wherein $R^6$ and R" are as defined above), after which this compound is reacted in the same manner as in step (3), followed by ring closure under acidic conditions, whereby there can be produced a compound of the present invention of the formula (i):

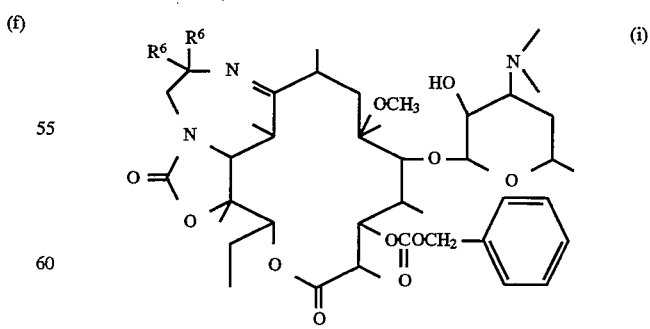

(i)

wherein $R^6$ is as defined above. Then, 10% Pd-C and ammonium formate are added to remove the benzyloxycarbonyl group at the 3-position to obtain a compound of the formula (j):

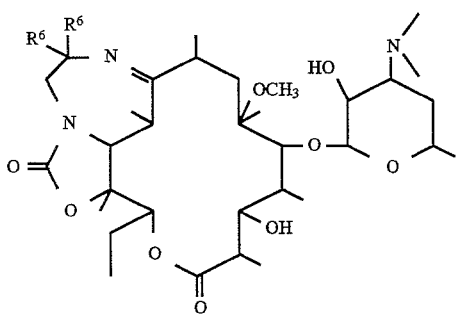

wherein $R^6$ is as defined above. The suitable inert solvent is the same as used in step (1).

Step 8:

The compound (j) obtained is reacted sequentially in the same manner as in steps (1), (2) and (3), whereby there can be produced a compound of the present invention of the formula (k):

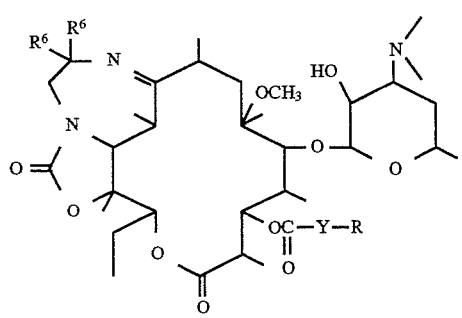

wherein R, $R^6$ and Y are as defined above.

Step (9):

The compound (g) is subjected to ring closure by addition of an amine of the formula $R^5$—$NH_2$ (wherein $R^5$ is as defined above) in a suitable solvent, after which the reaction product is reacted in the same manner as in step (3), whereby there can be produced a compound of the present invention of the formula (1):

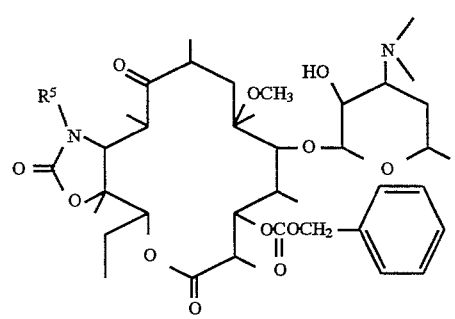

(wherein $R^5$ is as defined above) which is a 11,12-cyclic carbamate. Here, the suitable solvent is the same as used in step (6).

Step (10):

The compound obtained in step (9) is reacted with 10% Pd-C and ammonium formate in a lower alcohol at room temperature, after which the reaction product is reacted in the same manner as in steps (1), (2) and (3), whereby there can be produced a compound of the present invention of the formula (m):

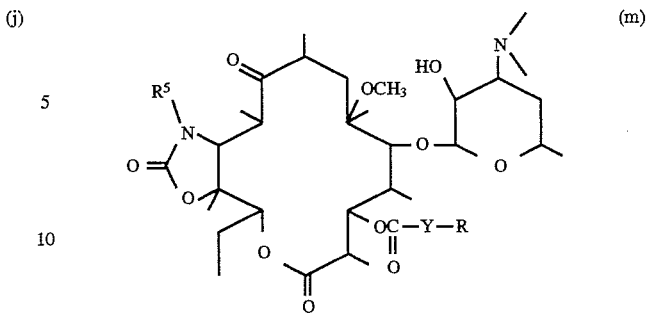

wherein R, $R^5$ and Y are as defined above.

[Production process 2]

Process using 6-O-methylerythromycin A 9-oxime as a starting material

Step (11):

6-O-methylerythromycin A 9-oxime is reacted with an acid in a lower alcohol at 0° C. to 30° C. to obtain a compound of the formula (n):

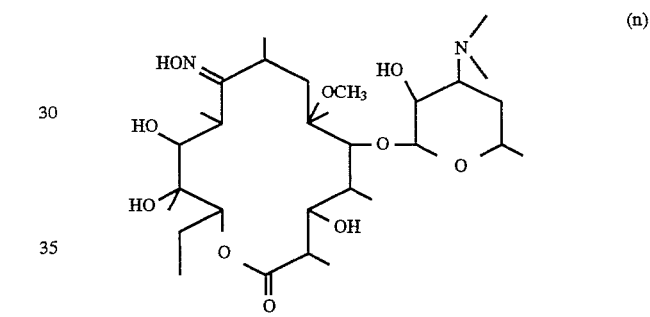

Here, the lower alcohol is the same as used in step (3). As the acid, there are used hydrochloric acid, hydrobromic acid, sulfuric acid, etc.

Step (12):

The compound obtained in step (11) is reacted with a reagent of the formula $R^4$—X (wherein $R^4$ and X are as defined above) and a base in an inert solvent at 0° C. to 30° C. to obtain a compound of the formula (o):

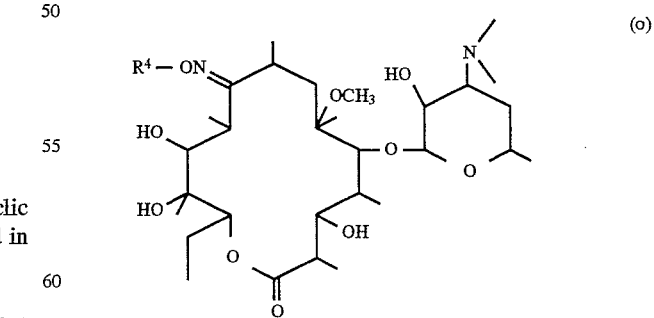

wherein $R^4$ is as defined above. Subsequently, this compound is reacted in the same manner as in steps (1), (2) and (3), whereby there can be produced a compound of the present invention of the formula (p):

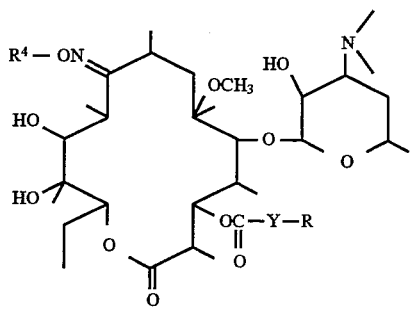

wherein R, R⁴ and Y are as defined above. Here, the inert solvent and the base are the same as used in step (6).

Step (13):

The compound of the formula (o) is reacted in the same manner as in steps (1) and (2) and then in the same manner as in step (4) to be converted into a 11,12-cyclic carbonate, which is reacted in the same manner as in step (3), whereby there can be produced a compound of the present invention of the formula (q):

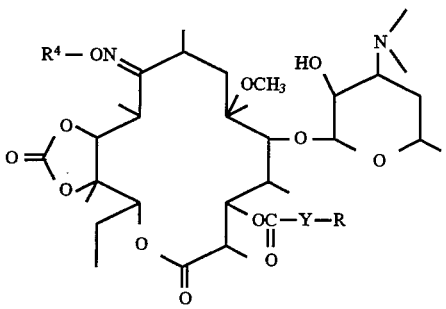

wherein R, R⁴ and Y are as defined above.

Step (14):

The compound obtained in step (11) is reacted in the same manner as in step (1) to protect the hydroxyl group at the 2'-position and the hydroxyl group of the oxime at the 9-position, after which the reaction product is reacted in the same manner as in steps (2) and then (3), whereby there can be produced a compound of the present invention of the formula (r):

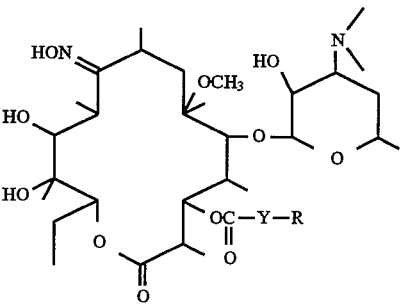

wherein R and Y are as defined above.

Step (15):

The compound obtained in step (11) is reacted in the same manner as in step (1) to protect the hydroxyl group at the 2'-position and the hydroxyl group of the oxime at the 9-position, after which the reaction product is reacted sequentially, in the same manner as in steps (2), (4) and (3), whereby there can be produced a compound of the present invention of the formula (s):

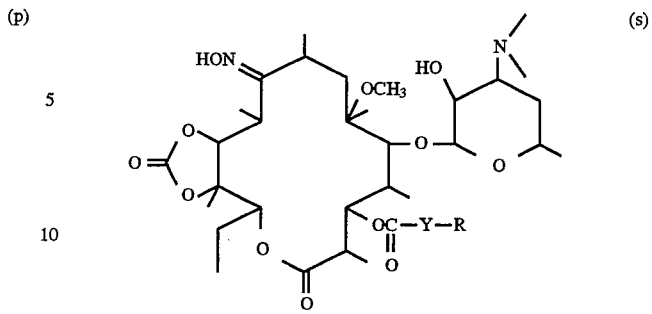

wherein R and Y are as defined above.

[Production process 3]

Process using 5-O-desosaminylerythronolide A 9-oxime as a starting material.

A compound of the present invention can be produced by reacting the starting material according to each of the steps of production process 2.

[Production process 4]

Process using 3-deoxy-3-oxo-5-O-desosaminyl-6-O-methylerythronolide A 9-oxime (described in EP 487411) as a starting material.

Step (16):

3-Deoxy-3-oxo-5-O-desosaminyl-6-O-methylerythronolide A 9-oxime is reacted with sodium borohydride in a lower alcohol at −20° C. to room temperature to obtain a compound of the formula (t):

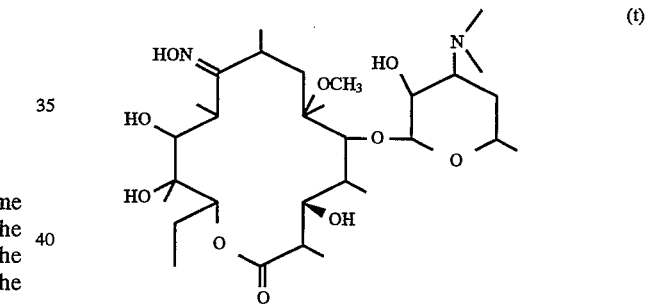

Here, the lower alcohol is the same as used in step (3). Then, the hydroxyl group at the 2'-position and the hydroxyl groups of the oxime at the 9-position are protected in the same manner as in step (1), after which the thus treated compound is reacted in the same manner as in step (4) to obtain a compound of the formula (u):

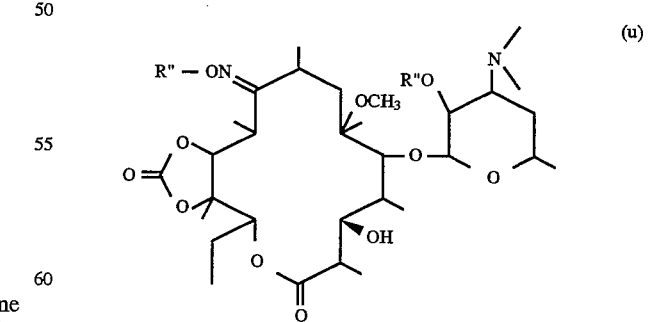

wherein R" is as defined above. Then, this compound is reacted in the same manner as in step (2), after which the protecting groups are removed in the same manner as in step (3), whereby there can be produced a compound of the present invention of the formula (v):

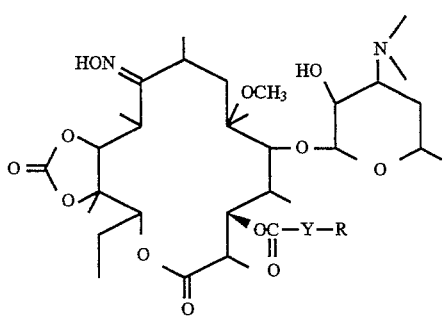

wherein R and Y are as defined above.

[Production process 5]

Process using 9-deoxo-9a-aza-9a-methyl-9a-homoerythromycin A as a starting material Step (17):

9-Deoxo-9a-aza-9a-methyl-9a-homoerythromycin A is first reacted with an acid in the same manner as in step (11) to obtain a compound of the formula (w):

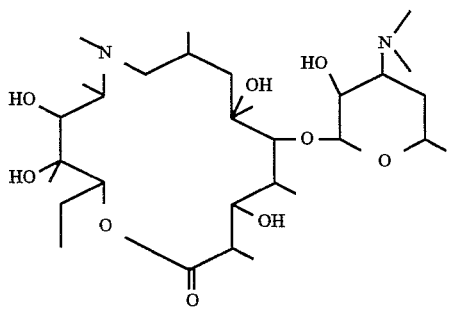

Subsequently, this compound is reacted in the same manner as in step (1) to protect the hydroxyl group at 2'-position, and then the thus treated compound is reacted in the same manner as in step (2) to obtain a compound of the formula (x):

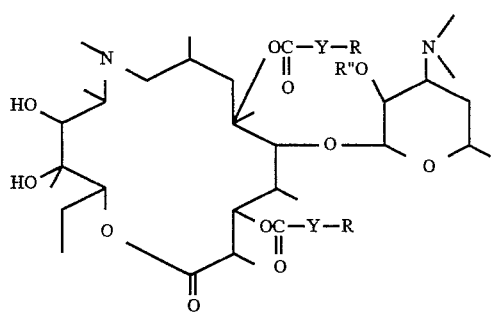

wherein R, R" and Y are as defined above. Next, this compound is reacted in the same manner as in step (3), whereby there can be produced a compound of the present invention of the formula (y):

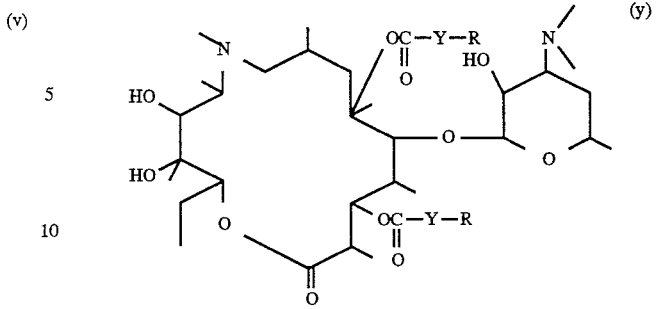

wherein R and Y are as defined above.

Step (18):

The compound of the formula (x) is converted into a cyclic carbonate in the same manner as in step (4) and the cyclic carbonate is reacted in the same manner as in step (3), whereby there can be produced a compound of the present invention of the formula (z):

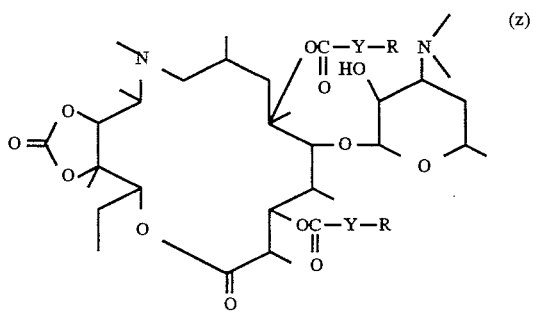

wherein R and Y are as defined above.

The compounds of the present invention can be administered orally or parenterally. Their pharmaceutical forms for administration are tablets, capsules, powders, troches, ointments, suspensions, suppositories, injections, etc. These can be prepared by conventional preparation techniques.

INDUSTRIAL APPLICABILITY

The compounds of the present invention have a strong antibacterial activity against erythromycin-sensitive bacteria and resistant bacteria. Therefore, the compounds of the present invention are useful as antibacterial agents for curing infectious diseases caused by bacteria in human beings and animals (including farm animals).

BEST MODE FOR CARRYING OUT THE INVENTION

The present invention is illustrated below in further detail with examples.

Example 1

Production of 3-O-(4-nitrophenyl)acetyl-5-O-desosaminyl-6-O-methylerythronolide A 9-oxime 11,12cyclic carbonate Production process (I)

(1) In 1 liter of 1N hydrochloric acid was dissolved 500 g (0.655 mole) of 6-O-methylerythromycin A 9-oxime, and the solution was allowed to stand at room temperature for 24 hours. Then, the solution was adjusted to pH 10 with an aqueous sodium hydroxide solution and the crystals precipitated were collected by filtration. The crystals were dissolved in dichloromethane, and the resulting solution was washed with a saturated aqueous sodium chloride solution and then dried over anhydrous magnesium sulfate. Subsequently, the dichloromethane was evaporated under reduced pressure and the residue was crystallized from methanol to obtain 259.8 g of 5-O-desosaminyl-6-O-methylerythronolide A 9-oxime as white powder.

m.p.; 257°–260° C. Mass (FAB) m/z; 605 [MH]$^{+1}$H-NMR (300 MHz, CDCl$_3$) δ (ppm); 1.42 (3H, s), 2.34 (6H, s), 2.99 (3H, s), 3.26 (1H, s), 3.57 (1H, s), 4.37 (1H, s), 4.42 (1H, d, J=7 Hz), 5.23 (1H, dd, J=11 Hz, 2 Hz), 7.43 (1H, broad-s) IR (KBr, cm$^{-1}$); 3523, 3370, 1712, 1188, 1169, 1085

(2) 5-O-desosaminyl-6-O-methylerythronolide A 9-oxime was obtained also by converting 5-0-desosaminyl-6-O-methylerythronolide A into an oxime by use of hydroxylamine hydrochloride and imidazole in methanol.

(3) Then, 10 g (16.56 mmoles) of 5-O-desosaminyl-6-O-methylerythronolide A 9-oxime was dissolved in dichloromethane (300 ml)-acetone (50 ml), and 6.95 g (82.8 mmoles) of sodium hydrogencarbonate and 3.67 ml (41.4 mmoles) of acetic anhydride were added under ice-cooling. The resulting mixture was slowly brought back to room temperature, stirred for 6.5 hours, and then extracted with dichloromethane, and the extract was washed with saturated sodium hydrogencarbonate and then a saturated aqueous sodium chloride solution. The dichloromethane layer was dried over anhydrous magnesium sulfate and the solvent was evaporated under reduced pressure to obtain 11.66 g of 2'-O-acetyl-5-O-desosaminyl-6-O-methylerythronolide A 9-acetoxime as white powder.

$^1$H-NMR (200 MHz, CDCl$_3$) δ (ppm); 2.06 (3H, s), 2.15 (3H, s), 2.26 (6H, s), 2.88 (3H, s)

(4) In 80 ml of dichloromethane was dissolved 5 g (7.73 mmoles) of the compound obtained in (3) above, and 13.3 ml (165 mmoles) of pyridine was added under ice-cooling. At the same temperature, 10 ml of 2.97 ml (24.8 mmoles) of trichloromethyl chloroformate in dichloromethane was added dropwise, after which the resulting mixture was slowly brought back to room temperature and stirred for 20 hours. Pieces of ice were added to the reaction mixture in small portions and the resulting mixture was adjusted to pH 7 with a sodium hydroxide solution, after which the solvent was evaporated under reduced pressure. The residue was extracted with ethyl acetate and the extract was washed with a saturated aqueous sodium chloride solution and then dried over anhydrous magnesium sulfate. The ethyl acetate was evaporated under reduced pressure and the residue was purified by a silica gel column chromatography (eluent; acetone: n-hexane: triethylamine=6–8:10:0.2) to obtain 4.56 g of 2'-O-acetyl-5-O-desosaminyl-6-O-methylerythronolide A 9-acetoxime 11,12-cyclic carbonate as a light-brown foamy substance.

Mass (FAB) m/z; 715 [MH]$^{+1}$H-NMR (300 MHz, CDCl$_3$) δ (ppm); 1.51 (3H, s), 2.06 (3H, s), 2.26 (6H, s), 2.30 (3H, s), 2.91 (3H, s), 4.59 (1H, d, J=7 Hz), 4.77 (1H, dd, J=9 Hz, 7 Hz), 5.16 (1H, dd, J=9 Hz, 2 Hz) IR (KBr, cm$^{-1}$); 3500, 1815, 1742, 1459, 1370, 1239, 1049

(5) In 40 ml of dichloromethane was dissolved 1.474 g (8.14 mmoles) of 4-nitrophenylacetic acid, and 1.14 ml (8.14 mmoles) of triethylamine was added. Under ice-cooling, 1.02 ml (8.14 mmoles) of pivaloyl chloride was added and the resulting mixture was stirred for 30 minutes, followed by adding thereto 2.25 ml (27.37 mmoles) of pyridine and 10 ml of a solution of 1.753 g (2.466 mmoles) of 2'-O-acetyl-5-O-desosaminyl-6-O-methylerythronolide A 9-acetoxime 11,12-cyclic carbonate in dichloromethane. The resulting mixture was stirred for 2 hours, after which the reaction solution was extracted with dichloromethane and the extract was washed with a saturated sodium hydrogencarbonate solution and a saturated aqueous sodium chloride solution. The dichloromethane layer was dried over anhydrous magnesium sulfate and the solvent was evaporated under reduced pressure, after which the crude product thus obtained was purified by a silica gel column chromatography (eluent; acetone: n-hexane: triethylamine=5:10:0.1) to obtain 1.81 g of a brown foamy substance.

1.8 Grams (2.06 mmoles) of this compound was dissolved in 25 ml of methanol and heated under reflux for 16 hours. The methanol was evaporated under reduced pressure and the residue was extracted with ethyl acetate. The extract was washed with a saturated aqueous sodium hydrogencarbonate solution and then a saturated aqueous sodium chloride solution and dried over anhydrous magnesium sulfate, after which the ethyl acetate was evaporated under reduced pressure. The crude product was purified by a silica gel column chromatography (eluent; chloroform: methanol: 25% ammonia=20:1:0.1) to obtain 1.47 g of the title compound as a light-yellow foamy substance.

m.p.; 151°–153° C. (light-yellow powder, recrystallized from methanol) Mass (FAB) m/z; 794 [MH]$^{+1}$H-NMR (200 MHz, CDCl$_3$) δ (ppm); 2.27 (6H, s), 3.03 (3H, s), 3.73, 3.74 (2H, ABq), 7.50, 7.56 (2H), 8.18, 8.24 (2H) IR (KBr, cm$^{-1}$); 1800, 1742, 1524, 1348, 1169, 1050

Production process (II)

5-O-desosaminyl-6-O-methylerythronolide A 9-oxime obtained according to (1) or (2) in production process (I) was reacted with trichloromethyl chloroformate by use of pyridine in dichloromethane in the same manner as in (4) in production process (I) to obtain 5-O-desosaminyl-6-O-methylerythronolide A 9-oxime 11,12-cyclic carbonate.

Mass (FAB) m/z; 631 [MH]$^{+1}$H-NMR (200 MHz, CDCl$_3$) δ (ppm); 2.50 (6H, s), 2.99 (3H, s), 4.51 (1H, d, J=7Hz), 4.93 (1H, s), 5.16 (1H, dd, J=12Hz, 3Hz), 8.28 (1H, broad-s)

This compound was acetylated in the same manner as in (3) to obtain 2'-O-acetyl-5-O-desosaminyl-6-O-methylerythronolide A 9-acetoxime 11,12-cyclic carbonate. Thereafter, the title compound was obtained in the same manner as in (5) in production process (I).

Example 2

Production of 3-O-(4-methoxyphenyl)acetyl-5-O-desosaminyl-6-O-methylerythronolide A (1) In 100 ml of acetone was dissolved 11.78 g (0.02 mole) of 5-O-desosaminyl-6-O-methylerythronolide A, followed by adding thereto 2.27 ml (0.024 mole) of acetic anhydride under ice-cooling, and the resulting mixture was stirred at room temperature for 6 hours. The acetone was evaporated under reduced pressure and the residue was extracted with dichloromethane. The dichloromethane layer was washed with a saturated sodium hydrogencarbonate solution and then a saturated aqueous sodium chloride solution and dried over anhydrous magnesium sulfate, after which the solvent was evaporated under reduced pressure. The residue was recrystallized from ether-n-hexane to obtain 12.17 g of 2'-O-acetyl-5-O-desosaminyl-6-O-methylerythronolide A as white powder.

m.p.; 158°–160° C. Mass (FAB) m/z; 632 [MH]$^{+1}$H-NMR (200 MHz, CDCl$_3$) δ (ppm); 2.07 (3H, s), 2.26 (6H, s), 2.95 (3H, s), 3.26 (1H, s), 3.96 (1H, s) IR (KBr, cm$^{-1}$); 3469, 1750, 1733, 1693

(2) 1.26 Grams (2.00 mmoles) of the compound obtained in (1) above was reacted with 1.097 g (6.6 mmoles) of p-methoxyphenylacetic acid, 0.91 ml (6.6 mmoles) of triethylamine, 0.81 ml (6.6 mmoles) of pivaloyl chloride, 1.8 ml (22.3 mmoles) of pyridine and 40 ml of dichloromethane for 24 hours in the same manner as in Example 1, (5) to obtain 620 mg of a white foamy substance. Then, this substance was heated under reflux in methanol for 8 hours, followed by after-treatment, and the crude product thus obtained was recrystallized from ethyl acetate to obtain 520 mg of the title compound as white powder.

m.p.; 191°–195° C. Mass (FAB) m/z; 738 [MH]$^{+1}$H-NMR (200 MHz, CDCl$_3$) δ (ppm); 2.39 (6H, s), 3.04 (3H, s), 3.80 (3H, s), 6.85–6.90 (2H, Ar-H), 7.18–7.31 (2H, Ar-H) IR (KBr, cm$^{-1}$); 1737, 1692, 1515, 1265, 1180, 1034

Example 3

Production of 3-O-(2,4-dinitrophenyl)acetyl-5-O-desosaminyl-6-O-methylerythronolide A 1.893 Grams (3 mmoles) of the compound obtained in Example 2, (1), 2.239 g (9.9 mmoles) of 2,4-dinitrophenylacetic acid, 1.24 ml (9.9 mmoles) of pivaloyl chloride, 1.39 ml (9.9 mmoles) of triethylamine, 2.75 ml (33.3 mmoles) of pyridine and 50 ml of dichloromethane were stirred for 24 hours in the same manner as in Example 1, (5) to be reacted, giving 620 mg of a brown oily substance. This substance was heated under reflux in methanol for 6.5 hours, followed by after-treatment, whereby 294 mg of the title compound was obtained as a brown foamy substance.

Mass (FAB) m/z; 798 [MH]$^{+1}$H-NMR (200 MHz, CDCl$_3$) δ (ppm); 2.30 (6H, s), 3.00 (3H, s), 3.95 (1H, s), 4.25, 4.27 (2H, ABq), 7.60, 7.64 (1H, Ar-H), 8.41, 8.42, 8.45, 8.46 (1H, Ar-H), 8.93, 8.95 (1H, Ar-H) IR (KBr, cm$^{-1}$); 3459, 1712, 1692, 1608, 1541, 1348, 1172, 1076, 1051

Example 4

Production of 3-O-(4-nitrophenyl)acetyl-5-O-desosaminyl-6-O-methylerythronolide A 1.894 Grams (3 mmoles) of the compound obtained in Example 2, (1), 1.793 g (9.9 mmoles) of 4-nitrophenylacetic acid, 1.24 ml (9.9 mmoles) of pivaloyl chloride, 1.39 ml (9.9 mmoles) of triethylamine, 2.75 ml (33.3 mmoles) of pyridine and 50 ml of dichloromethane were stirred for 4 hours in the same manner as in Example 1, (5) to be reacted, followed by heating under reflux in methanol for 2.5 hours and after-treatment, whereby 1.66 g of the title compound was obtained as a yellow foamy substance.

m.p.; 134°–136° C. (light-yellow powder, recrystallized from ethyl acetate) Mass (FAB) m/z; 753 [MH]$^{+1}$H-NMR (200 MHz, CDCl$_3$) δ (ppm); 2.26 (6H, s), 3.04 (3H, s), 7.52, 7.56 (2H, Ar-H), 8.19, 8.23 (2H, Ar-H) IR (KBr, cm$^{-1}$); 3470, 1731, 1693, 1608, 1525, 1459, 1348, 1171, 1110, 1074

Example 5

Production of 3-O-phenylthioacetyl-5-O-desosaminyl-6-O-methylerythronolide A 1.26 Grams (2 mmoles) of the compound obtained in Example 2, (1) and 1.01 g (6 mmoles) of phenylthioacetic acid were stirred for 24 hours in the same manner as in Example 1, (5) to be reacted, after which protecting groups were removed to obtain 750 mg of the title compound as a white foamy substance.

m.p.; 161°–163° C. (white powder, recrystallized from ethyl acetate) Mass (FAB) m/z; 740 [MH]$^+$ $^1$H-NMR (200 MHz, CDCl$_3$) δ (ppm); 2.22 (6H, s), 3.01 (3H, s), 3.21 (1H, s), 3.75 (2H, ABq), 3.94 (1H, s), 7.19–7.45 (5H, m, aromatic proton) IR (KBr, cm$^{-1}$); 3469, 1738, 1692, 1172, 1110, 1075, 1034

Example 6

Production of 3-O-(2-pyridyl)acetyl-5-O-desosaminyl-6-O-methylerythronolide A 1.26 Grams (2 mmoles) of the compound obtained in Example 2, (1) and 1.146 g (6.6 mmoles) of 2-pyridylacetic acid hydrochloride were reacted in the same manner as in Example 1, (5) to obtain 1.12 g of a yellow foamy substance. This substance was heated under reflux in methanol for 5 hours, followed by after-treatment, whereby 930 mg of the title compound was obtained as a yellow foamy substance.

m.p.; 189°–190.5° C. (light-yellow powder, recrystallized from ether-n-hexane) Mass (FAB) m/z; 709 [MH]$^{+1}$H-NMR (200 MHz, CDCl$_3$) δ (ppm); 2.28 (6H, s), 3.03 (3H, s), 3.93 (2H), 3.94 (1H, s), 7.17–7.24 (1H), 7.35, 7.38 (1H), 7.62–7.72 (1H), 8.50–8.54 (1H) IR (KBr, cm$^{-1}$); 3460, 1741, 1693, 1171, 1110, 1076, 1034

Example 7

Production of 3-O-(3-thienyl)acetyl-5-O-desosaminyl-6-O-methylerythronolide A 1.26 Grams (2 mmoles) of the compound obtained in Example 2, (1) and 853 mg (6 mmoles) of 3-thiopheneacetic acid were reacted in the same manner as in Example 1, (5) to obtain 270 mg of the title compound as a white foamy substance.

m.p.; 130°–132° C. (white powder, recrystallized from acetone-n-hexane) Mass (FAB) m/z; 714 [MH]$^{+1}$H-NMR (200 MHz, CDCl$_3$), δ (ppm); 2.27 (6H, s), 3.05 (3H, s), 3.21 (1H, s), 3.72 (2H, s), 4.92 (1H, s), 7.08–7.12 (1H), 7.20–7.29 (2H) IR (KBr, cm$^{-1}$); 3436, 1737, 1693, 1633, 1172, 1077

Example 8

Production of 3-O-[3-(4-methoxyphenyl)propionyl]-5-O-desosaminyl-6-O-methylerythronolide A 1.262 Grams (2 mmoles) of the compound obtained in Example 2, (1) and 1.081 g (6 mmoles) of 3-(4-methoxyphenyl)propionic acid were reacted in the same manner as in Example 1, (5) to obtain 80 mg of the title compound as a white foamy substance.

m.p.; 56°–60° C. (foam) Mass (FAB) m/z; 752 [MH]$^+$ $^1$H-NMR (200 MHz, CDCl$_3$) δ (ppm); 2.28 (6H, s), 3.03 (3H, s), 3.77 (3H, s), 6.79, 6.82 (2H), 7.08–7.14 (2H) IR (KBr, cm$^{-1}$); 3462, 1739, 1692, 1614, 1515, 1249, 1171

Example 9

Production of 3-O-(4-nitrophenyl)acetyl-5-O-desosaminyl-6-O-methylerythronolide A 11,12 cyclic carbonate (1) In 500 ml of dichloromethane was dissolved 50 g (84.8 mmoles) of the compound obtained in Example 2, (1), and 102.6 ml (1.27 moles) of pyridine was added under ice-cooling. At the same temperature, 40 ml of a solution of 25.4 ml (212 mmoles) of trichloromethyl chloroformate in dichloromethane was added dropwise, and the resulting mixture was stirred for 5.5 hours. Cold water and a saturated sodium hydrogencarbonate solution were added to the reaction solution in small portions, followed by extraction with dichloromethane. The dichloromethane layer was washed with a saturated sodium hydrogencarbonate solution and then a saturated aqueous sodium chloride solution and dried over anhydrous magnesium sulfate, after which the solvent was evaporated under reduced pressure.

The residue was purified by a silica gel column chromatography (eluent; acetone: n-hexane: triethylamine= 6–10:10:0.2) to obtain 41.93 g of 2'-O-acetyl-5-O-desosaminyl-6-O-methylerythronolide A 11,12 cyclic carbonate as a white foamy substance.

$^1$H-NMR (200 MHz, CDCl$_3$) δ (ppm); 2.05 (3H, s), 2.25 (6H, s), 2.92 (3H, s), 4.57 (1H, d, J=9 Hz), 4.74 (1H, s), 4.75 (1H, dd, J=10 Hz, 9 Hz), 5.13 (1H, dd, J=12 Hz, 2 Hz)

(2) By reacting 5-O-desosaminyl-6-O-methylerythronolide A by use of trichloromethyl chloroformate and pyridine in dichloromethane in the same manner as in (1) above, its 11,12-cyclic carbonate was obtained.

$^1$H-NMR (200 MHz, CDCl$_3$) δ (ppm); 1.51 (3H, s), 2.50 (6H, s), 2.94 (3H, s), 4.51 (1H, d, J=7 Hz), 4.76 (1H, s), 5.14 (1H, dd, J=11 Hz, 3 Hz)

(3) 2'-O-acetyl-5-O-desosaminyl-6-O-methylerythronolide A 11,12 cyclic carbonate was obtained also by acetylating the compound obtained in (2) above, on the hydroxyl group at the 2'-position with acetic anhydride in acetone.

(4) From 1.62 g (2.466 mmoles) of the compound obtained in (3) above, 1.474 g (8.14 mmoles) of 4-nitrophenylacetic acid, 1.14 ml (8.14 mmoles) of triethylamine, 1.02 ml (8.14 mmoles) of pivaloyl chloride, 2.25 ml (27.37 mmoles) of pyridine and 50 ml of dichloromethane, 1.12 g of light-yellow powder was obtained by reacting them in the same manner as in Example 1, (5). 1.12 Grams (1.364 mmoles) of this compound was heated under reflux in 30 ml of methanol for 2 hours, followed by after-treatment and recrystallization from ethyl acetate, whereby 447 mg of the title compound was obtained as white powder.

m.p.; 126°–128° C. Mass (FAB) m/z; 779 [MH]$^+$ $^1$H-NMR (200 MHz, CDCl$_3$) δ (ppm); 2.43 (6H, s), 2.99 (3H, s), 3.85 (2H, ABq), 4.75 (1H, s), 7.54, 7.58 (2H, Ar-H), 8.18, 8.22 (2H, Ar-H) IR (KBr, cm$^{-1}$); 3458, 1813, 1743

Example 10

Production of 3-O-(4-chlorophenyl)acetyl-5-O-desosaminyl-6-O-methylerythronolide A 11,12 cyclic carbonate Using 970 mg (1.476 mmoles) of the compound obtained in Example 9, (3), 831 mg (4.871 mmoles) of 4-chlorophenylacetic acid, 0.68 ml (4,871 mmoles) of triethylamine, 0.61 ml (4.871 mmoles) of pivaloyl chloride, 1.35 ml (16.384 mmoles) of pyridine and 40 ml of dichloromethane, 270 mg of a white foamy substance was obtained by reacting them for 18 hours in the same manner as in Example 1, (5). 260 Milligrams of (0.321 mmole) of this compound was heated under reflux in 15 ml of methanol for 3.5 hours, followed by after-treatment, whereby 150 mg of the title compound was obtained as white powder.

m.p.; 112°–115° C. Mass (FAB) m/z; 768 [MH]$^+$ $^1$H-NMR (200 MHz, CDCl$_3$) δ (ppm); 2.49 (6H, s), 2.99 (3H, s), 3.25 (1H, dd), 3.69 (2H, ABq), 4.75 (1H, s), 5.06 (1H, d), 7.33 (4H, Ar-H) IR (KBr, cm$^{-1}$); 1817, 1743, 1716, 1169, 1109, 1082, 1044

Example 11

Production of 3-O-(4-methoxyphenyl)acetyl-5-O-desosaminyl-6-O-methylerythronolide A 11,12-cyclic carbonate By using 1.31 mg (2.0 mmoles) of the compound obtained in Example 9, (3), 1.097 g (6.6 mmoles) of 4-methoxyphenylacetic acid, 0.81 ml (6.6 mmoles) of pivaloyl chloride, 0.91 ml (6.6 mmoles) of triethylamine, 1.8 ml (22.3 mmoles) of pyridine and 20 ml of dichloromethane, 660 mg of a white foamy substance was obtained in the same manner as in Example 1, (5). 640 Milligrams of this substance was heated under reflux in 15 ml of methanol for 16 hours, followed by after-treatment, whereby 360 mg of the title compound was obtained as a white foamy substance.

m.p.; 92°–96° C. (foam) Mass (FAB) m/z; 764 [MH]$^+$ $^1$H-NMR (200 MHz, CDCl$_3$) δ (ppm); 2.38 (6H, s), 3.00 (3H, s), 3.65 (2H, s), 3.81 (3H, s), 4.75 (1H, s), 6.87 (2H, Ar-H), 7.28 (2H, Ar-H) IR (KBr, cm$^{-1}$); 1813, 1743, 1169, 1044

Example 12

Production of 11-amino-9-N,11-N-cyclic ethylene-9-deoxo-11-deoxy-5-O-desosaminyl-3-O-(4-nitrophenyl) acetyl-6-O-methylerythronolide A 9-imine 11-N,12-O-cyclic carbamate (1) In 230 ml of dichloromethane was dissolved 42.5 g (67.3 mmoles) of the compound obtained in Example 2, (1), and 81.4 ml (1.01 moles) of pyridine was added under ice-cooling. At the same temperature, 20 ml of a solution of 20.2 ml (168 mmoles) of trichloromethyl chloroformate in dichloromethane was added dropwise, and the resulting mixture was stirred for 3 hours, after which 72.7 ml (673 mmoles) of benzyl alcohol was added dropwise over a period of 30 minutes. After stirring at room temperature for another 16 hours, pieces of ice were added in small portions, and the resulting mixture was adjusted to pH 7 with a sodium hydroxide solution. The dichloromethane was evaporated under reduced pressure and the residue was extracted with ethyl acetate. The ethyl acetate layer was washed with a saturated aqueous sodium chloride solution, dried over anhydrous magnesium sulfate, and concentrated to a solvent volume of 300 ml under reduced pressure. The crystals precipitated were collected by filtration to obtain 38.7 g of 2'-O-acetyl-5-O-desosaminyl-3-O-benzyloxycarbonyl-6-O-methylerythronolide A 11, 12cyclic carbonate.

Mass (FAB)m/z; 792 [MH]$^+$ $^1$H-NMR (300 MHZ, CDCl$_3$) δ (ppm); 1.49 (3H, s), 2.07 (3H, s), 2.25 (6H, s), 2.99 (3H, s), 4.70 (1H, s), 5.21 (2H, s), 7.35–7.46 (5H, m) IR (KBr, cm$^{-1}$); 1821, 1746, 1715, 1267, 1241

(2) In 100 ml of dimethylformamide-tetrahydrofuran (1:1) was dissolved 10 g (12.6 mmoles) of the compound obtained in (1) above, followed by adding thereto 8.18 g (50.4 mmoles) of 1,1'-carbonyldiimidazole and 1.11 g (27.8 mmoles) of 60% sodium hydride, and the resulting mixture was stirred at room temperature for 0.5 hour. The tetrahydrofuran was evaporated under reduced pressure and water was poured into the residue, followed by extraction with ethyl acetate. The organic layer was washed with water and then a saturated aqueous sodium chloride solution and dried over anhydrous magnesium sulfate. The solvent was evaporated to obtain 11.5 g of 2'-O-acetyl-5-O-desosaminyl-10, 11-anhydro-3-O-benzyloxycarbonyl-12-O-imidazolylcarbonyl-6-O-methylerythronolide A as a white foamy substance.

(3) In 50 ml of acetonitrile was dissolved 5 g (5.9 mmoles) of the compound obtained in (2) above, followed by adding thereto 4.0 ml (59.8 mmoles) of ethylenediamine, and the resulting mixture was stirred at room temperature for 1 hour. The solvent was evaporated under reduced pressure, and after-treatment was carried out in the same manner as in (2) above. The solvent was evaporated to obtain 5.4 g of 2'-O-acetyl-5-O-desosaminyl-ll-(2-amino)ethylamino-3-O-benzyloxycarbonyl-11-deoxy-6-O-methylerythronolide A 11-N,12-O-cyclic carbamate.

(4) In 50 ml of methanol was dissolved 5.4 g (6.5 mmoles) of the compound obtained in (3) above and the resulting solution was heated under reflux for 1 hour to carry out deacetylation at the 2'-position. Purification by a silica gel column chromatography (eluent; chloroform: methanol: aqueous ammonia=10:1:0.1) gave 4.4 g of a white foamy substance. Then, 4.4 g (5.6 mmoles) of this compound was dissolved in 40 ml of ethanol, followed by adding thereto 0.64 ml (11.2 mmoles) of acetic acid, and the resulting mixture was stirred overnight at room temperature. The solvent was evaporated under reduced pressure and a 2N sodium hydroxide solution and water were added to the residue, followed by extraction with ethyl acetate. The organic layer was dried over anhydrous magnesium sulfate, followed by evaporating. The residue was purified by a silica gel column chromatography (eluent; chloroform: methanol: aqueous ammonia=10:1:0.1) to obtain 3.66 g of 11-amino- 3-O-benzyloxycarbonyl-9-N,11-N-cyclic ethylene-9-deoxo-11-deoxy-5-O-desosaminyl-6-O-methylerythronolide A 9-imine 11-N,12-O-cyclic carbamate.

Mass (FAB) m/z; 774 [MH]$^{+1}$H-NMR (300 MHz, CDCl$_3$) δ (ppm); 2.21 (6H, s, 3'-N(CH$_3$)$_2$), 3.09 (3H, s, 6-OCH$_3$), 5.20 (2H, s, —OCOCH$_2$—), 7.32–7.45 (5H, m, Ar-H) $^{13}$C-NMR (75 MHz, CDCl$_3$) δ (ppm); 40.3 (3'-N(CH$_3$)$_2$), 49.5 (6-OCH$_3$), 69.9 (—OCOCH$_2$—)

(5) In 30 ml of methanol was dissolved 3.61 g (4.7 mmoles) of the compound obtained in (4) above, followed by adding thereto 0.72 mg of 10% Pd-C and 2.94 g (46.7 mmoles) of ammonium formate, and the resulting mixture was stirred at room temperature for 45 minutes. The catalyst was filtered off and the filtrate was concentrated, after which a 2N sodium hydroxide solution and water were added to the residue, followed by extraction with chloroform. The organic layer was subjected to after-treatment in the same manner as in (2) above, and then the solvent was evaporated under reduced pressure to obtain 3.26 g of 11-amino-9-N,11-N-cyclic ethylene-9-deoxo-11-deoxy-5-O-desosaminyl-6-O-methylerythronolide A 9-imine 11-N,12-O-cyclic carbamate.

(6) In 30 ml of acetone was dissolved 3 g (4.7 mmoles) of the compound obtained in (5) above, followed by adding thereto 0.73 ml (7.7 mmoles) of acetic anhydride, and the reaction was carried out at room temperature for 2.5 hours. The acetone was evaporated under reduced pressure and then after-treatment was carried out in the same manner as in (2) above. The extraction solvent was evaporated, after which the residue was purified by a silica gel column chromatography (eluent; chloroform: methanol: aqueous ammonia=20:1:0.1) to obtain 1.2 g of 2'-O-acetyl-5-O-desosaminyl-11-amino- 9-N,11-N-cyclic ethylene-9-deoxo11-deoxy-6-O-methylerythronolide A 9-imine 11-N,12-O-cyclic carbamate.

(7) In 5 ml of methylene chloride were dissolved 558 mg (3.1 mmoles) of 4-nitrophenylacetic acid, 0.43 ml (3.1 mmoles) of triethylamine and 0.38 ml (3.1 mmoles) of pivaloyl chloride, and the resulting solution was stirred at −15° C. for 20 minutes. To this solution was added dropwise 5 ml of a solution in methylene chloride of 0.7 g (1.0 mmole) of the compound obtained in (6) above, at room temperature. The resulting mixture was subjected to reaction as it was for 2 hours, after which a 2N sodium hydroxide solution and water were added to the reaction mixture and after-treatment was carried out in the same manner as in (2) above. The solvent was evaporated and the residue was purified by a silica gel column chromatography (eluent; chloroform: methanol aqueous ammonia=30:1:0.1) to obtain 0.78 g of a 2'-O-acetyl-3-O-(4-nitrophenyl) acetate ester as a white foamy substance. 0.71 Gram of the compound obtained was dissolved in 10 ml of methanol and heated under reflux for 1 hour. After the reaction, the methanol was evaporated and the residue was purified by a silica gel column chromatography (eluent; chloroform: methanol: aqueous ammonia= 20:1:0.1) and then crystallized from chloroform-n-hexane to obtain 0.52 g of the title compound.

m.p.; 243°–246° C. Mass (FAB) m/z; 803 [MH]$^{+1}$H-NMR (300 MHz, CDCl$_3$) δ (ppm); 1.34 (3H, s), 1.43 (3H, s), 2.27 (6H, s), 3.07 (3H, s), 7.51–7.55, 8.19–8.20 (4H, Ar-H) $^{13}$C-NMR (75 MHz, CDCl$_3$) δ (ppm); 40.4 (3'-N (CH$_3$)$_2$), 41.1 (3-OCOCH$_2$—), 42.6, 49.5 (NCH$_2$CH$_2$N), 49.5 (6-OCH$_3$), 123.8, 130.5, 140.9, 147.4 (ph), 156.3 (11-NCOO-12), 169.8 (3-OCOCH$_2$—) IR (KBr, cm$^{-1}$); 3436, 2975, 1759, 1744

Example 13

Production of 11-amino-9-N,11-N-cyclic (1,1-dimethyl) ethylene-9-deoxo-11-deoxy-5-O-desosaminyl-3-O-(4-nitrophenyl)acetyl-6-O-methylerythronolide A 9-imine 11-N,12-O-cyclic carbamate (1) In 60 ml of acetonitrile was dissolved 6.45 g (7.7 mmoles) of the compound obtained in Example 12, (2), followed by adding thereto 8.0 ml (76.3 mmoles) of 1,2-diamino-2-methylpropane, and the resulting mixture was stirred at 50° C. for 2 hours and then at room temperature overnight. After-treatment was carried out in the same manner as in Example 12, (3) to obtain 6.8 g of 2'-O-acetyl-5-O-desosaminyl-11-(2-amino-2-methyl)-propylamino-3-O-benzyloxycarbonyl-11-deoxy-6-O-methylerythronolide A, 11-N,12-O-cyclic carbamate, which was white and foamy.

(2) In 60 ml of methanol was dissolved 6.8 g (7.9 mmoles) of the compound obtained in (1), and the reaction was carried out in the same manner as in Example 12, (4) to obtain 6.4 g of a compound deacetylated at the 2'-position. Then, 6.4 g (7.8 mmoles) of this compound was dissolved in 60 ml of ethanol, followed by adding thereto 0.89 ml (15.5 mmoles) of acetic acid, and the resulting mixture was heated under reflux for 50 hours. After the reaction, after-treatment was carried out in the same manner as in Example 12, (4) to obtain 3.3 g of 11-amino-3-O-benzyloxycarbonyl-9-N,11-N-cyclic (1,1-dimethyl)ethylene-9-deoxo-11-deoxy-5-O-desosaminyl-6-O-methylerythronolide A 9-imine 11-N,12-O-cyclic carbamate.

Mass (FAB) m/z; 802 [MH]$^+$ (3) In 30 ml of methanol was dissolved 3.3 g (4.1 mmoles) of the compound obtained in (2) above, followed by adding thereto 660 mg of 10% Pd-C and 2.7 g (42.9 mmoles) of ammonium formate, and the reaction was carried out in the same manner as in Example 12, (5) to obtain 2.7 g of 11-amino-9-N,11-N-cyclic(1,1-dimethyl)-ethylene-9-deoxo-11-deoxy-5-O-desosaminyl-6-O-methylerythronolide A 9-imine 11-N,12-O-cyclic carbamate.

(4) In 30 ml of acetone was dissolved 2.7 g (4.0 mmoles) of the compound obtained in (3) above, followed by adding thereto 0.66 ml (7.0 mmoles) of acetic anhydride, and the reaction was carried out in the same manner as in Example 12, (6) to obtain 2.5 g of 2'-O-acetyl-5-O-desosaminyl-11-amino-9-N,11-N-cyclic (1,1-dimethyl)ethylene-9-deoxo-11-deoxy-6-O-methylerythronolide A 9-imine 11-N,12-O-cyclic carbamate.

(5) By using 797 mg (4.4 mmoles) of 4-nitrophenylacetic acid, 0.61 ml (4.4 mmoles) of triethylamine, 0.54 ml (4.4 mmoles) of pivaloyl chloride and 1.0 g (1.4 moles) of the compound obtained in (4) above, and reacting them in the same manner as in Example 12, (7), 1.22 g of 2'-O-acetyl-3-O-(4-nitrophenyl)acetyl was obtained. By reacting this compound in the same manner as in Example 12, (7), 0.93 g of the title compound was obtained.

Mass (FAB) m/z; 830 [MH]$^{+1}$H-NMR (300 MHz, CDCl$_3$) δ (ppm); 1.43 (3H, s), 2.28 (6H, s), 3.08 (3H, s), 7.52–7.55, 8.20–8.23 (4H, Ar-H) $^{13}$C-NMR (75 MHz, CDCl$_3$) δ (ppm); 40.4 (3'-N(CH$_3$)$_2$), 41.1 (3-OCOCH$_2$—), 49.6 (6-OCH$_3$), 123.8, 130.5, 140.9,147.3 (ph), 156.5 (11-NCOO-12), 69.9 (3-OCOCH$_2$—) IR (KBr, cm$^{-1}$); 3436, 2974, 1746

Example 14

Production of 3-O-(4-nitrophenyl)acetyl-5-O-desosaminylerythronolide A 9-oxime

Production process (I)

(1) In methanol was dissolved 50 g (66.84 moles) of erythromycin A 9-oxime, followed by adding thereto 1 liter of 1N hydrochloric acid, and the solution was allowed to stand at room temperature for 24 hours. Then, the solution was adjusted to pH 10 with a sodium hydroxide solution, and the crystals precipitated were collected by filtration. The crystals were dissolved in dichloromethane and the resulting solution was washed with a saturated aqueous sodium chloride solution and then dried over anhydrous magnesium sulfate. Subsequently, the dichloromethane was evaporated under reduced pressure and the residue was crystallized from methanol to obtain 31.5 g of 5-O-desosaminylerythronolide A 9-oxime as white powder.

(2) In 150 ml of dichloromethane was dissolved 10 g (16.56 mmoles) of the compound obtained in (1) above, and 6.95 g (82.8 mmoles) of sodium hydrogencarbonate and 3.67 ml (41.4 mmoles) of acetic anhydride were added under ice-cooling. The resulting mixture was slowly brought back to room temperature, stirred for 6.5 hours, and then extracted with dichloromethane, and the extract was washed with saturated sodium hydrogencarbonate and then a saturated aqueous sodium chloride solution. The dichloromethane layer was dried over anhydrous magnesium sulfate and the solvent was evaporated under reduced pressure to obtain 12.7 g of 2'-O-acetyl-5-O-desosaminylerythronolide A 9-acetoxime as white powder.

(3) In 50 ml of dichloromethane was dissolved 1.51 g (8.3 mmoles) of 4-nitrophenylacetic acid, and 1.29 ml (8.3 mmoles) of triethylamine was added. Under ice-cooling, 1.16 ml (8.3 mmoles) of pivaloyl chloride was added and the resulting mixture was stirred for 30 minutes, after which 1.12 ml (13.9 mmoles) of pyridine and 10 ml of a solution in dichloromethane of 1.87 g (2.78 mmoles) of the compound obtained in (2) above were added. After stirring for 2 hours, the reaction mixture was extracted with dichloromethane and the extract was washed with a saturated sodium hydrogencarbonate solution and a saturated aqueous sodium chloride solution. The dichloromethane layer was dried over anhydrous magnesium sulfate and the solvent was evaporated under reduced pressure, after which the crude product thus obtained was purified by a silica gel column chromatography (eluent; acetone: n-hexane: triethylamine= 5:10:0.1) to obtain 1.35 g of brown foamy 2'-O-acetyl-3-O-(4-nitrophenyl)acetyl-5-O-desosaminylerythronolide A 9-acetoxime.

(4) The aforesaid compound was dissolved in 15 ml of methanol and heated under reflux for 6 hours. The methanol was evaporated under reduced pressure and the residue was extracted with ethyl acetate. The extract was washed with a saturated aqueous sodium hydrogencarbonate solution and then a saturated aqueous sodium chloride solution and dried over anhydrous magnesium sulfate, and the ethyl acetate was evaporated under reduced pressure. The crude product was purified by a silica gel column chromatography (eluent; chloroform: methanol: 25% ammonia=20:1:0.1) to obtain 1.06 g of the title compound as a light-yellow foamy substance.

m.p.; 144°–146° C. (light-yellow powder, recrystallized from methanol) Mass (FAB) m/z; 754 [MH]$^+$ $^1$H-NMR (200 MHz, CDCl$_3$) δ (ppm); 2.32 (6H, s), 3.10 (1H, s), 3.80, 3.81 (2H), 3.99 (1H, d, J=9 Hz), 4.49 (1H, s), 7.51, 7.55 (2H), 8.17, 8.21 (2H)

Example 15

Production of 3-O-(4-nitrophenyl)acetyl-5-O-desosaminylerythronolide A 9-oxime 11,12-cyclic carbonate (1) In 30 ml of dichloromethane was dissolved 1.04 g (1.244 mmoles) of the compound obtained in Example 14, (3) and 2.0 ml (24.88 mmoles) of pyridine was added under ice-cooling. At the same temperature, 10 ml of a solution of 0.38 ml (3.11 mmoles) of trichloromethyl chloroformate in dichloromethane was added dropwise, and the resulting mixture was slowly brought back to room temperature and stirred for 7.5 hours. Pieces of ice were added to the reaction mixture in small portions and the mixture thus obtained was adjusted to pH 7 with a sodium hydroxide solution, after which the solvent was evaporated under reduced pressure. The residue was extracted with ethyl acetate, and the extract was washed with a saturated aqueous sodium chloride solution and then dried over anhydrous magnesium sulfate. The ethyl acetate was evaporated under reduced pressure and the residue was purified by a silica gel column chromatography (eluent; acetone: n-hexane: triethylamine= 6–8:10:0.2) to obtain 790 mg of a light-brown foamy substance.

(2) The compound obtained in (1) above was dissolved in 15 ml of methanol and heated under reflux for 4 hours. The methanol was evaporated under reduced pressure and the residue was extracted with ethyl acetate. The extract was washed with a saturated aqueous sodium hydrogencarbonate solution and then a saturated aqueous sodium chloride solution and dried over anhydrous magnesium sulfate, and the ethyl acetate was evaporated under reduced pressure. The crude product was purified by a silica gel column chromatography (eluent; chloroform: methanol: 25% ammonia=20:1:0.1) to obtain 510 mg of the title compound as a light-yellow foamy substance.

Mass (FAB) m/z; 780 [MH]$^+$ $^1$H-NMR (200 MHz, CDCl$_3$) δ (ppm); 2.35 (6H, s), 4.98 (1H, s), 5.19 (1H, d, J=9 Hz), 7.51, 7.56 (2H), 8.16, 8.21 (2H)

Example 16

Production of 3-O-(4-nitro)benzyloxycarbonyl-5-O-desosaminyl-6-O-methylerythronolide A 11,12-cyclic carbonate In 20 ml of dichloromethane was dissolved 1.90 g (3.0 mmoles) of the compound obtained in Example 2, (1), followed by adding thereto 3.63 ml (45 mmoles) of pyridine and 0.90 ml (7.5 mmoles) of trichloromethyl chloroformate under ice-cooling, and the resulting mixture was stirred for 2 hours. Under ice-cooling, 4.59 g (30 mmoles) of 4-nitrobenzyl alcohol was added and then stirred for 1 hour. Pieces of ice and 1.5 g of sodium hydrogencarbonate were added, followed by extraction with ethyl acetate. The extract was purified by a silica gel column chromatography (eluent; hexane: acetone: triethylamine=10:6:0.1) to obtain 0.31 g of the title compound which was yellow and foamy.

m.p.; 152°–154° C. (crystallized from methanol) Mass (FAB) m/z; 795 [MH]$^+$ IR (KBr, cm$^{-1}$); 3436, 1812, 1752, 1715 $^1$H-NMR (300 MHz, CDCl$_3$) δ (ppm); 2.21 (6H, s), 3.01 (3H, s), 5.23, 5.34 (2H, ABq, J=13 Hz)

Example 17

Production of 3-O-phenylacetyl-5-O-desosaminyl-6-O-methylerythronolide A

In 6 ml of pyridine was dissolved 1.262 g (2 mmoles) of the compound obtained in Example 2, (1), followed by adding thereto 0.66 ml (5 mmoles) of phenylacetyl chloride and 122 mg (1 mmole) of 4-dimethylaminopyridine under ice-cooling, and the resulting mixture was stirred at room temperature for 22 hours. The mixture was extracted with ethyl acetate, and the extract was washed with a saturated aqueous sodium chloride solution and then purified by a silica gel column chromatography (eluent; hexane: acetone: triethylamine=10:4:0.05) to obtain 730 mg of 2'-O-acetyl-3-O-phenylacetyl-5-O-desosaminyl-6-O-methylerythronolide A. This compound was heated under reflux in 10 ml of methanol for 6 hours to be deacetylated, whereby there was obtained 490 mg of the title compound which was light-yellow and foamy.

Mass (FAB) m/z; 708 [MH]$^+$ IR (KBr, cm$^{-1}$); 3464, 1739, 1693, 1172 $^1$H-NMR (200 MHz, CDCl$_3$) δ (ppm); 2.26 (6H, s), 3.02 (3H, s), 3.69, 3.71 (2H), 3.95 (1H, s), 5.07 (1H, d, J=11 Hz), 7.28–7.37 (5H)

Example 18
Production of 3-O-(pentafluorophenyl)acetyl-5-O-desosaminyl-6-O-methylerythronolide A (1) In 30 ml of dichloromethane was dissolved 1.029 g (4.55 mmoles) of pentafluorophenylacetic acid, and 0.64 ml (4.55 mmoles) of triethylamine was added. Under ice-cooling, 0.57 ml (4.55 mmoles) of pivaloyl chloride was added and then stirred for 30 minutes, followed by adding thereto 0.63 ml (7.59 mmoles) of pyridine and 10 ml of a solution in dichloromethane of 957 mg (1.517 mmoles) of the compound obtained in Example 2, (1). After stirring for 2 hours, the reaction solution was extracted with dichloromethane and the extract was washed with a saturated sodium hydrogencarbonate solution and a saturated aqueous sodium chloride solution. The dichloromethane layer was dried over anhydrous magnesium sulfate and the solvent was evaporated under reduced pressure, after which the crude product thus obtained was purified by a silica gel column chromatography (eluent; acetone: n-hexane: triethylamine= 5:10:0.1) to obtain 810 mg of white crystalline powder.

(2) The compound obtained in (1) above was dissolved in 30 ml of methanol and heated under reflux for 4 hours. The methanol was evaporated under reduced pressure and the residue was extracted with ethyl acetate. The extract was washed with a saturated aqueous sodium hydrogencarbonate solution and then a saturated aqueous sodium chloride solution and thereafter dried over anhydrous magnesium sulfate, and the ethyl acetate was evaporated under reduced pressure. The crude product was purified by a silica gel column chromatography (eluent; chloroform: methanol: 25% ammonia=20:1:0.1) to obtain 670 mg of the title compound which was light-yellow and foamy.

Mass (FAB) m/z; 798 [MH]$^{+1}$H-NMR (200 MHz, CDCl$_3$) δ (ppm); 1.29 (3H, s), 2.27 (6H, s), 3.01 (3H, s), 5.11 (1H, d, J=11 Hz)

Example 19
Production of 3-O-(2-amino-4-thiazolyl)acetyl-5-O-desosaminyl-6-O-methylerythronolide A (1) In 30 ml of tetrahydrofuran was dissolved 948 mg (6 mmoles) of (2-amino-4-thiazolyl)acetic acid, and 0.84 ml (6 mmoles) of triethylamine was added. Under ice-cooling, 0.75 ml (6 mmoles) of pivaloyl chloride was added and then stirred for 30 minutes, followed by adding thereto 1.66 ml (20 mmoles) of pyridine and 10 ml of a solution in dichloromethane of 1.26 g (2 mmoles) of the compound obtained in Example 2, (1). After stirring for 2 hours, the reaction mixture was extracted with ethyl acetate and thereafter after-treatment was carried out in the same manner as in Example 18, (1) to obtain 330 mg of a brown oily substance.

(2) The compound obtained in (1) was dissolved in 5 ml of methanol and the resulting solution was stirred at room temperature for 24 hours, after which the solvent was evaporated to obtain 224 mg of the title compound which was white and foamy.

Mass (FAB) m/z; 730 [MH]$^{+1}$H-NMR (200 MHz, CDCl$_3$) δ (ppm); 1.31 (3H, s), 2.28 (6H, s), 3.05 (3H, s), 3.65 (2H, s), 3.95 (1H, s), 4.34 (1H, d, J=8 Hz), 5.10 (1H, d, J=11 Hz), 5.21 (2H, broad-s), 6.37 (1H, s)

Example 20
Production of 3-O-(4-nito)cinnamoyl-5-O-desosaminyl-6-O-methylerythronolide A (1) In 10 ml of dichloromethane was dissolved 1.26 g (2 mmoles) of the compound obtained in Example 2, (1), followed by adding thereto 1.16 g (6 mmoles) of 4-nitrocinnamic acid, 1.15 g (6 mmoles) of 1-ethyl-3-(3-dimethylaminopropyl)carbodiimide hydrochloride and 240 mg (2 mmoles) of 4-dimethylaminopyridine under ice-cooling, and the resulting mixture was stirred at room temperature for 24 hours. Thereafter, after-treatment was carried out in the same manner as in Example 18, (1) to obtain 570 mg of a light-yellow foamy substance.

(2) The compound obtained in (1) was dissolved in 5 ml of methanol and the resulting solution was stirred at room temperature for 18 hours, after which the solvent was evaporated to obtain 413 mg of the title compound which was yellow and foamy.

Mass (FAB) m/z; 765 [MH]$^{+1}$H-NMR (200 MHz, CDCl$_3$) δ (ppm); 2.06 (6H, s), 3.08 (3H, s), 3.99 (1H, s), 6.65 (1H, d, J=16 Hz), 7.70, 7.75 (2H), 7.79 (1H, d, J=16Hz), 8.25, 8.30 (2H)

Example 21
Production of 3-O-[3-(3-pyridyl)acryloyl]-5-O-desosaminyl-6-O-methylerythronolide A (1) In 10 ml of dichloromethane was dissolved 1.26 g (2 mmoles) of the compound obtained in Example 2, (1), followed by adding thereto 895 mg (6 mmoles) of 3-(3-pyridyl)acrylic acid, 1.15 g (6 mmoles) of 1-ethyl-3-(3-dimethylaminopropyl)carbodiimide hydrochloride and 240 mg (2 mmoles) of 4-dimethylaminopyridine under ice-cooling, and the resulting mixture was stirred at room temperature for 24 hours. Thereafter, after-treatment was carried out in the same manner as in Example 18, (1).

(2) The compound obtained in (1) was dissolved in 30 ml of methanol and the resulting solution was stirred at room temperature for 19 hours, after which the solvent was evaporated to obtain 690 mg of the title compound which was white and foamy.

Mass (FAB) m/z; 721 [MH]$^{+1}$H-NMR (200 MHz, CDCl$_3$) δ (ppm); 2.07 (6H, s), 3.07 (3H, s), 3.99 (1H, s), 5.23 (1H, d, J=10 Hz), 6.61 (1H, d, J=16 Hz), 7.33–7.40 (1H, m), 7.76 (1H, d, J=16 Hz), 7.86–7.92 (1H, m), 8.62–8.67 (1H, m), 8.78–8.81 (1H, m)

Example 22
Production of 3-O-(3-indolyl)acetyl-5-O-desosaminyl-6-O-methylerythronolide A (1) In 60 ml of dichloromethane was dissolved 1.26 g (2 mmoles) of the compound obtained in Example 2, (1), followed by adding thereto 1.05 g (6 mmoles) of β-indoleacetic acid, 1.15 g (6 mmoles) of 1-ethyl-3-(3-dimethylaminopropyl)carbodiimide hydrochloride and 244 mg (2 mmoles) of 4-dimethylaminopyridine under ice-cooling, and the resulting mixture was stirred at room temperature for 24 hours. Thereafter, after-treatment was carried out in the same manner as in Example 18, (1) to obtain 530 mg of a brown and foamy substance.

(2) To the compound 520 mg obtained in (1) were added 10 ml of methanol and 2 ml of a saturated sodium hydrogencarbonate solution, and the resulting mixture was stirred at room temperature for 2 hours, after which the solvent was evaporated to obtain 390 mg of the title compound as light-brown powder.

Mass (FAB) m/z; 747 [MH]$^{+1}$H-NMR (200 MHz, CDCl$_3$) δ (ppm); 1.28 (3H, s), 2.19 (6H, s), 3.07 (3H, s), 3.90 (2H), 3.96 (1H, s), 5.13 (1H, d, J=10 Hz), 7.10–7.26 (2H), 7.35–7.40 (2H), 7.63–7.68 (1H, 8.15 (1H)

Example 23
Production of 3-O-(2-naphthyl)acetyl-5-O-desosaminyl-6-O-methylerythronolide A 11,12-cyclic carbonate (1) In 30 ml of dichloromethane was dissolved 1.117 g (6 mmoles) of β-naphthylacetic acid, and 0.84 ml (6 mmoles) of triethylamine was added. Under ice-cooling, 0.75 ml (6 mmoles) of pivaloyl chloride was added and then stirred for 30 minutes, followed by adding thereto 1.65 ml (20 mmoles) of pyridine and 10 ml of a solution in dichloromethane of 1.31 g (2 mmoles) of the compound obtained in Example 9, (1). After stirring at room temperature for 23 hours, after-treatment was carried out in the same manner as in Example 18, (1) to obtain 690 mg of a compound.

(2) The compound obtained in (1) above was dissolved in 10 ml of methanol and heated under reflux for 2.5 hours. Thereafter, after-treatment was carried out in the same manner as in Example 18, (2) to obtain 550 mg of the title compound as white powder.

Mass (FAB) m/z; 784 [MH]$^{+1}$H-NMR (200 MHz, CDCl$_3$) δ (ppm); 1.49 (3H, s), 2.29 (6H, s), 3.02 (3H, s), 3.89, 3.90 (2H), 4.77 (1H, s), 5.02 (1H, d, J=11 Hz), 7.45–7.57 (3H), 7.79–7.87 (4H)

Example 24

Production of 3-O-(4-biphenyl)acetyl-5-O-desosaminyl-6-O-methylerythronolide A 11,12-cyclic carbonate (1) In 30 ml of dichloromethane was dissolved 1.274 g (6 mmoles) of 4-biphenylacetic acid, and 0.84 ml (6 mmoles) of triethylamine was added. Under ice-cooling, 0.75 ml (6 mmoles) of pivaloyl chloride was added and then stirred for 30 minutes, followed by adding thereto 1.65 ml (20 mmoles) of pyridine and 10 ml of a solution in dichloromethane of 1.31 g (2 mmoles) of the compound obtained in Example 9, (1). After stirring at room temperature for 19 hours, after-treatment was carried out in the same manner as in Example 18, (1) to obtain 580 mg of a light-yellow and powdery compound.

(2) The compound obtained in (1) above was dissolved in 10 ml of methanol and heated under reflux for 3 hours. Thereafter, after-treatment was carried out in the same manner as in Example 18, (2) to obtain 490 mg of the title compound which was light-yellow and foamy.

$^1$H-NMR (200 MHz, CDCl$_3$) δ (ppm); 2.21 (6H, s), 3.01 (3H, s), 3.90 (1H, d, J=7 Hz), 4.76 (1H, s), 5.10 (1H, d, J=11 Hz), 7.30–7.49 (5H), 7.55–7.61 (4H)

Example 25

Production of 3-O-(4-trifluoromethyl)phenyl-acetyl-5-O-desosaminyl-6-O-methylerythronolide A 11,12cyclic carbonate (1) In 30 ml of dichloromethane was dissolved 1.225 g (6 mmoles) of (4-trifluoromethyl)phenylacetic acid, and 0.84 ml (6 mmoles) of triethylamine was added. Under ice-cooling, 0.75 ml (6 mmoles) of pivaloyl chloride was added and then stirred for 30 minutes, followed by adding thereto 0.83 ml (10 mmoles) of pyridine and 10 ml of a solution in dichloromethane of 1.31 g (2 mmoles) of the compound obtained in Example 9, (1). After stirring at room temperature for 24 hours, after-treatment was carried out in the same manner as in Example 18, (1) to obtain 1.06 mg of a light-yellow and powdery compound.

(2) The compound obtained in (1) above was dissolved in 30 ml of methanol and the resulting solution was stirred at room temperature for 24 hours. Thereafter, after-treatment was carried out in the same manner as in Example 18, (2) to obtain 660 mg of the title compound as white powder.

$^1$H-NMR (200 MHz, CDCl$_3$) δ (ppm); 1.30 (3H, s), 1.48 (3H, s), 2.26 (6H, s), 3.00 (3H, s), 3.87 (1H, d, J=6 Hz), 4.76 (1H, s), 5.09 (1H, d, J=10 Hz), 7.47, 7.51 (2H), 7.58, 7.62 (2H)

Example 26

Production of 3-O-(4-aminophenyl)acetyl-5-O-desosaminyl-6-O-methylerythronolide A 9-oxime 11,12-cyclic carbonate In 20 ml of methanol was suspended 1 g (1.26 mmoles) of the compound of Example 1, and 599 mg (2.52 mmoles) of nickel chloride hexahydrate and 191 mg (5.04 mmoles) of sodium borohydride were added in small portions under ice-cooling. The resulting mixture was stirred for 2.5 hours and then extracted with ethyl acetate. The extract was treated by a conventional method and purified by a silica gel column chromatography (eluent; chloroform: methanol: aqueous ammonia=20:1:0.05) to obtain 710 mg of the title compound which was yellow and foamy.

Mass (FAB) m/z; 764 [MH]$^{+1}$H-NMR (200 MHz, CDCl$_3$) δ (ppm); 2.32 (6H, s), 3.03 (3H, s), 3.56, 3.57 (2H), 4.90 (1H, s), 5.02 (1H, d, J=11 Hz), 6.61, 6.66 (2H), 7.10, 7.15(2H)

Example 27

Production of 3-O-(4-dimethylaminophenyl)-acetyl-5-O-desosaminyl-6-O-methylerythronolide A 9-oxime 11,12-cyclic carbonate In 3 ml of ethanol was dissolved 260 mg (0.34 mmole) of the compound of Example 26, followed by adding thereto 0.58 ml (7.4 mmoles) of 35% formaldehyde and 0.02 ml (0.41 mmole) of 99% formic acid, and the resulting mixture was heated under reflux for 6 hours. The mixture was made basic with aqueous ammonia and extracted with ethyl acetate, after which the extract was subjected to after-treatment by a conventional method. Purification by a silica gel column chromatography (eluent; chloroform: methanol: aqueous ammonia=20: 1:0.05) gave 123 mg of the title compound which was light-yellow and foamy.

Mass (FAB) m/z; 792 [MH]$^{+1}$H-NMR (200 MHz, CDCl$_3$) δ (ppm); 2.47 (6H, broad-s), 2.93 (6H, s), 3.03 (3H, s), 6.67, 6.72 (2H), 7.19, 7.23 (2H), 7.49 (1H, broad-s)

Example 28

Production of 3-O-(4-nitrophenyl)acetyl-5-O-desosaminyl-6-O-methylerythronolide A 9-[0-(2chlorobenzyl)oxime]

(1) In 30 ml of N,N-dimethylformamide was dissolved 3.02 g (5 mmoles) of the compound obtained in Example 1, (1), followed by adding thereto 0.94 ml (7.5 mmoles) of 2-chlorobenzyl chloride and 240 mg (6 mmoles) of 60% sodium hydride under ice-cooling. After stirring for 5 hours, the reaction solution was extracted with ethyl acetate and the extract was washed with a saturated aqueous sodium chloride solution. The ethyl acetate layer was dried over anhydrous magnesium sulfate and the solvent was evaporated under reduced pressure. The residue was purified by a silica gel column chromatography (eluent; chloroform: methanol: 25% aqueous ammonia=20:1:0.1) to obtain 1.91 g of white and foamy 5-O-desosaminyl-6-O-methylerythronolide A 9-[O-(2-chlorobenzyl)oxime].

(2) The compound obtained in (1) above was acetylated in the same manner as in Example 2, (1) to obtain 1.13 g (1.466 mmoles) of white and foamy 2'-O-acetyl-5-O-desosaminyl-6-O-methylerythronolide A 9-[O(2-chlorobenzyl)oxime].

(3) In 30 ml of dichloromethane was dissolved 0.797 g (4.398 mmoles) of 4-nitrophenylacetic acid, and 0.68 ml (4.398 mmoles) of triethylamine was added. Under ice-cooling, 0.61 ml (4.398 mmoles) of pivaloyl chloride was added and then stirred for 30 minutes, followed by adding thereto 1.18 ml (14.66 mmoles) of pyridine and 10 ml of a solution in dichloromethane of the compound obtained in (2) above. Thereafter, after-treatment was carried out in the same manner as in Example 1, (5) to obtain 1.19 g of a compound.

(4) In 5 ml of methanol was dissolved 200 mg of the compound obtained in (3) above, and heated under reflux for 2 hours. Thereafter, after-treatment was carried out in the same manner as in Example 18, (2) to obtain 180 mg of the title compound which was light-brown and foamy.

Mass (FAB) m/z; 892 [MH]$^{+1}$H-NMR (200 MHz, CDCl$_3$) δ (ppm); 2.30 (6H, s), 2.94 (3H, s), 3.82, 3.85 (2H), 4.90

(1H, s), 5.12, 5.17 (2H), 7.21–7.44 (4H), 7.52, 7.57 (2H), 8.19, 8.24 (2H) IR (KBr, cm$^{-1}$); 3436, 1741, 1525, 1348, 1171

Example 29

Production of 3-O-(4-nitrophenyl)acetyl-5-O-desosaminyl-6-O-methylerythronolide A 9-[O-(2chlorobenzyl)oxime] 11,12-cyclic carbonate (1) In 20 ml of dichloromethane was dissolved 990 mg (1.042 mmoles) of the compound obtained in Example 28, (2), and 1.68 ml (20.84 mmoles) of pyridine was added under ice-cooling. At the same temperature, 10 ml of a solution of 0.31 ml (2.61 mmoles) of trichloromethyl chloroformate in dichloromethane was added dropwise, and the resulting mixture was slowly brought back to room temperature and stirred for 6.5 hours. Thereafter, after-treatment was carried out in the same manner as in Example 1, (4) to obtain 480 mg of a yellow and powdery compound.

(2) The compound obtained in (1) above was dissolved in 5 ml of methanol and heated under reflux for 2 hours. Thereafter, after-treatment was carried out in the same manner as in Example 18, (2), followed by recrystallization from acetone, whereby 350 mg of the title compound was obtained as yellow powder.

Mass (FAB) m/z; 918 [MH]$^{+1}$H-NMR (200 MHz, CDCl$_3$) δ (ppm); 2.26 (6H, s), 2.74 (3H, s), 3.81, 3.82 (2H), 4.83 (1H, s), 5.15, 5.21 (2H, ABq, J=13 Hz), 7.15–7.36 (4H), 7.50, 7.55 (2H), 8.18, 8.23 (2H) IR (KBr, cm$^{-2}$); 3467, 1811, 1746, 1607, 1524, 1458, 1348, 1168

Example 30

Production of 3-O-(4-nitrophenyl)acetyl-5-O-desosaminyl-6-O-methylerythronolide A 9-[O-(2dimethylaminoethyl)oxime]

(1) In 120 ml of tetrahydrofuran was dissolved 15 g (24.8 mmoles) of the compound obtained in Example 1, (1), followed by adding thereto 5.08 g (24.8 mmoles) of 2-bromoethylamine hydrobromide and 3.30 g (112 mmoles) of 95% potassium hydroxide powder, and the resulting mixture was stirred at room temperature for 3 hours. Then, 5.08 g (24.8 mmoles) of 2-bromoethylamine hydrobromide and 3.30 g (112 mmoles) of 95% potassium hydroxide powder were added, and the mixture thus obtained was stirred for 20 hours. The solvent was evaporated, followed by extraction with ethyl acetate and purification by a silica gel column chromatography (eluent; chloroform: methanol: aqueous ammonia=9:1:0.1), whereby 10.90 g (16.8 mmoles) of 5-O-desosaminyl-6-O-methylerythronolide A 9-[O-(2aminoethyl)oxime] as colorless caramel.

(2) In 50 ml of ethanol was dissolved the compound obtained in (1) above, followed by adding thereto 6.09 ml (71.0 mmoles) of 35% formaldehyde and 2.03 ml (53.2 mmoles) of 99% formic acid, and the resulting mixture was heated under reflux for 1 hour. The solvent was evaporated, followed by extraction with ethyl acetate. The carmel thus obtained was purified by a silica gel column chromatography (eluent; chloroform: methanol: aqueous ammonia= 9:1:0.1) to obtain 5.54 g of 5-O-desosaminyl-6-O-methylerythronolide A 9-[O-(2-dimethylaminoethyl)oxime] as colorless crystalline powder.

(3) The compound obtained in (2) above was reacted in the same manner as in Example 2, (1) to obtain 5.57 g of 2'-O-acetyl-5-O-desosaminyl-6-O-methylerythronolide A 9-[O-(dimethylaminoethyl)oxime].

(4) In 30 ml of dichloromethane was dissolved 1.359 g (7.5 mmoles) of 4-nitrophenylacetic acid, and 1.16 ml (7.5 mmoles) of triethylamine was added. Under ice-cooling, 1.04 ml (7.5 mmoles) of pivaloyl chloride was added and then stirred for 30 minutes, followed by adding thereto 1.01 ml (12.5 mmoles) of pyridine and 10 ml of a solution in dichloromethane of 1.79 g (2.5 mmoles) of the compound obtained in (3) above. After stirring at room temperature for 5.5 hours, the reaction solution was extracted with ethyl acetate and the extract was subjected to after-treatment in the same manner as in Example 18, (1) to obtain 1.30 g of a compound.

(5) In 5 ml of methanol was dissolved 300 mg of the compound obtained in (4) above, and the resulting solution was stirred at room temperature for 24 hours. Thereafter after-treatment was carried out in the same manner as in Example 18, (2), followed by recrystallization from ethyl acetate, whereby 157 mg of the title compound was obtained.

$^1$H-NMR (200 MHz, CDCl$_3$) δ (ppm); 2.27 (12H, s), 3.06 (3H, s), 4.04–4.12 (2H, m), 5.08 (1H, d, J=11 Hz), 7.50, 7.55 (2H), 8.18, 8.23 (2H)

Example 31

Production of 3-O-(4-nitrophenyl)acetyl-5-O-desosaminyl-6-O-methylerythronolide A 9-[O-(2dimethylaminoethyl)oxime] 11,12-cyclic carbonate (1) In 25 ml of dichloromethane was dissolved 1.0 g (1.136 mmoles) of the compound obtained in Example 30, (4), and 1.83 ml (22.72 mmoles) of pyridine was added under ice-cooling. At the same temperature, 10 ml of a solution of 0.34 ml (2.84 mmoles) of trichloromethyl chloroformate in dichloromethane was added dropwise, and the resulting mixture was slowly brought back to room temperature and stirred for 6 hours. Thereafter, after-treatment was carried out in the same manner as in Example 1, (4) to obtain 270 mg of a compound.

(2) The compound obtained in (1) above was dissolved in 4 ml of methanol and the resulting solution was stirred at room temperature for 20 hours. Thereafter, after-treatment was carried out in the same manner as in Example 18,(2) to obtain 244 mg of the title compound which was white and foamy.

Mass (FAB) m/z; 865 [MH]$^{+1}$H-NMR (200 MHz, CDCl$_3$) δ (ppm); 1.34 (3H, s), 1.49 (3H, s), 2.26 (6H, s), 2.35 (6H, s), 3.00 (3H, s), 4.14–4.21 (2H, m), 4.87 (1H, s), 5.07 (1H, s, J=11 Hz), 7.51, 7.56 (2H), 8.18, 8.23 (2H)

Example 32

Production of 2'-O-{2-[2-(2-methoxyethoxy)ethoxy]ethoxy}carbonyl-3-O-(4-nitrophenyl)acetyl-5-O-desosaminyl-6-O-methylerythronolide A (1) In 100 ml of acetone was dissolved 5.90 g (0.01 mole) of 5-O-desosaminyl-6-O-methylerythronolide A, followed by adding thereto 4.2 g (0.05 mole) of sodium hydrogencarbonate and 2.72 g (0.012 mole) of 2-[2-(2-methoxyethoxy)ethoxy]ethyl chloroformate under ice-cooling, and the resulting mixture was stirred for 5 hours. The acetone was evaporated, followed by extraction with ethyl acetate, whereby 6.57 g (8.43 mmoles) of 2'-methoxyethoxyethoxyethoxycarbonyl compound was obtained.

(2) In 120 ml of dichloromethane was dissolved 4.581 g (25.29 mmoles) of 4-nitrophenylacetic acid, and 3.92 ml (25.29 mmoles) of triethylamine was added. Under ice-cooling, 3.50 ml (25.29 mmoles) of pivaloyl chloride was added and then stirred for 30 minutes, followed by adding thereto 6.80 ml (84.3 mmoles) of pyridine and 10 ml of a solution in dichloromethane of the compound obtained in (1) above. After stirring at room temperature for 4 hours, after-treatment was carried out in the same manner as in Example 1, (5) to obtain 6.63 g of the title compound which was brown and foamy.

$^1$H-NMR (200 MHz, CDCl$_3$) δ (ppm); 2.26 (6H, s), 3.00 (3H, s), 3.24 (1H, s), 3.36 (3H, s), 4.27–4.39 (2H, m), 4.49

(1H, dd, J=10 Hz, 7 Hz), 5.05 (1H, d, J=11 Hz), 7.55, 7.60 (2H), 8.20, 8.25 (2H)

Example 33

Production of 2'-O-{2-[2-(2-methoxyethoxy)ethoxy]ethoxy}carbonyl-3-O-(4-nitrophenyl)acetyl-5-O-desosaminyl-6-O-methylerythronolide A 11,12-cyclic carbonate In 70 ml of dichloromethane was dissolved 3 g (3.18 mmoles) of the compound of Example 32, and 5.14 ml (63.6 mmoles) of pyridine was added under ice-cooling. At the same temperature, 10 ml of a solution of 0.96 ml (7.95 mmoles) of trichloromethyl chloroformate in dichloromethane was added dropwise, and the resulting mixture was slowly brought back to room temperature and stirred for 24 hours. Thereafter, after-treatment was carried out in the same manner as in Example 1, (4) to obtain 970 mg of the title compound as light-brown powder.

$^1$H-NMR (200 MHz, CDCl$_3$) δ (ppm); 2.25 (6H, s), 2.98 (3H, s), 3.39 (3H, s), 4.49 (1H, dd, J=10 Hz, 7 Hz), 5.05 (1H, d, J=11 Hz), 7.55, 7.60 (2H), 8.20, 8.25 (2H)

Example 34

Production of 3-O-(4-nitrophenyl)acetyl-5-O-desosaminylerythronolide A 9-[O-(methoxyethoxymethyl)oxime]

(1) 8.1 Grams of erythromycin A 9-[O-(methoxyethoxymethyl)oxime] was reacted in the same manner as in Example 1, (1) to obtain 5.0 g of 5-O-desosaminylerythronolide A 9-[O-(methoxyethoxymethyl)oxime] as a white foamy substance.

$^1$H-NMR (200 MHz, CDCl$_3$) δ (ppm); 1.43 (3H, s), 2.25 (6H, s), 2.63 (1H, s), 3.18 (1H, s), 3.39 (3H, s), 4.23 (1H, s), 5.18 (2H, s)

(2) 4.9 Grams of the compound obtained in (1) above was acetylated in the same manner as in Example 2, (1) to obtain 4.88 g of 2'-O-acetyl-5-O-desosaminylerythronolide A 9-[O-(methoxyethoxymethyl)oxime] as a white foamy substance.

(3) In 50 ml of dichloromethane was dissolved 1.51 g (8.34 mmoles) of 4-nitrophenylacetic acid, and 1.29 ml (8.34 mmoles) of triethylamine was added. Under ice-cooling, 1.16 ml (8.34 mmoles) of pivaloyl chloride was added and then stirred for 30 minutes, followed by adding thereto 1.12 ml (13.9 mmoles) of pyridine and 10 ml of a solution in dichloromethane of 2 g of the compound obtained in (2) above. After stirring at room temperature for 5 hours, after-treatment was carried out in the same manner as in Example 1, (5) to obtain 2.32 g of a compound.

(4) In 5 ml of ethanol, 500 mg of the compound obtained in (3) above was stirred for 22 hours to be deacetylated, whereby 390 mg of the title compound was obtained as a light-brown foamy substance.

Mass (FAB) m/z; 842 [MH]$^{+1}$H-NMR (200 MHz, CDCl$_3$) δ (ppm); 2.29 (6H, s), 3.43 (3H, s), 4.35 (1H, s), 5.17 (2H), 7.51, 7.56 (2H), 8.17, 8.22 (2H) IR (KBr, cm$^{-1}$); 3447, 1742, 1524, 1348, 1168

Example 35

Production of 3-O-(4-nitrophenyl)acetyl-5-O-desosaminylerythronolide A 9-[O-(methoxyethoxymethyl)oxime] 11,12-cyclic carbonate (1) In 40 ml of dichloromethane was dissolved 1.73 g (1.96 mmoles) of the compound obtained in Example 34, (3), and 3.16 ml (39.2 mmoles) of pyridine was added under ice-cooling. At the same temperature, 10 ml of a solution of 0.59 ml (4.90 mmoles) of trichloromethyl chloroformate in dichloromethane was added dropwise, and the resulting mixture was slowly brought back to room temperature and stirred for 24 hours. Thereafter, after-treatment was carried out in the same manner as in Example 1, (4) to obtain 710 mg of a light-brown foamy compound.

(2) The compound obtained in (1) above was stirred in 10 ml of methanol for 28 hours to be deacetylated, whereby 660 mg of the title compound was obtained as a light-brown foamy substance.

Mass (FAB) m/z; 868 [MH]$^{+1}$H-NMR (200 MHz, CDCl$_3$) δ (ppm); 2.27 (6H, s), 3.44 (3H, s), 5.00 (1H, s), 5.25 (2H), 7.50, 7.55 (2H), 8.18, 8.23 (2H) IR (KBr, cm$^{-1}$); 3436, 1812, 1747, 1524, 1348

Example 36

Production of 3,6-di-O-(4-nitrophenyl)acetyl-5-O-desosaminyl-9-deoxo-9a-aza-9a-methyl-9a-homoerythronolide A (1) 3.62 Grams of 9-deoxo-9a-aza-9a-methyl-9a-homoerythromycin A was treated in the same manner as in Example 1, (1) to obtain 2.53 g of 5-O-desosaminyl-9-deoxo-9a-aza-9a-methyl-9a-homoerythronolide A as a white foamy substance.

Mass (FAB) m/z; 591 [MH]$^{+1}$H-NMR (300 MHz, CDCl$_3$) δ (ppm); 1.06 (3H, s), 1.31 (3H, s), 2.24 (6H, s), 2.36 (3H, s) IR (KBr, cm$^{-1}$); 3436, 1714, 1459, 1378, 1172

(2) 2.44 Grams of the compound obtained in (1) above was acetylated in the same manner as in Example 2, (1) to obtain 2.21 g of 2'-O-acetyl-5-O-desosaminyl-9-deoxo-9a-aza-9a-methyl-9a-homoerythronolide A as white powder.

(3) In 10 ml of dichloromethane was dissolved 690 mg (3.81 mmoles) of 4-nitrophenylacetic acid, and 0.59 ml (3.81 mmoles) of triethylamine was added. Under ice-cooling, 0.53 ml (3.81 mmoles) of pivaloyl chloride was added and then stirred for 30 minutes, followed by adding thereto 0.51 ml (6.35 mmoles) of pyridine and 10 ml of a solution in dichloromethane of 800 mg (1.27 mmoles) of the compound obtained in (2) above. After stirring at room temperature for 6 hours, after-treatment was carried out in the same manner as in Example 1, (5) to obtain 800 mg of a brown and foamy compound.

(4) In 2 ml of methanol, 150 mg of the compound obtained in (3) above was stirred for 24 hours to be deacetylated, whereby 91 mg of the title compound was obtained as a light-yellow foamy substance.

Mass (FAB) m/z; 917 [MH]$^{+1}$H-NMR (200 MHz, CDCl$_3$) δ (ppm); 2.27 (6H, s), 2.40 (3H, s), 4.14 (1H, d, J=7 Hz), 7.51, 7.56 (4H), 8.16, 8.19, 8.21, 8.23 (4H)

Example 37

Production of 3,6-di-O-(4-nitrophenyl)acetyl-5-O-desosaminyl-9-deoxo-9a-aza-9a-methyl-9a-homoerythronolide A 11,12-cyclic carbonate (1) In 15 ml of dichloromethane was dissolved 630 mg (0.69 mmole) of the compound obtained in Example 36, (3), and 1.27 ml (12 mmoles) of pyridine was added under ice-cooling. At the same temperature, 10 ml of a solution of 0.24 ml (1.50 mmoles) of trichloromethyl chloroformate in dichloromethane was added dropwise, and the resulting mixture was slowly brought back to room temperature and stirred for 20 hours. Thereafter, after-treatment was carried out in the same manner as in Example 1, (4) to obtain 320 mg of a brown and oily compound.

(2) The compound obtained in (1) above was stirred in 10 ml of methanol at room temperature to be deacetylated, whereby 170 mg of the title compound was obtained as a light-yellow foamy substance.

Mass (FAB) m/z; 943 [MH]$^{+1}$H-NMR (300 MHz, CDCl$_3$) δ (ppm); 1.50 (3H, s), 1.57 (3H, s), 2.12 (3H, s), 2.31 (6H, s), 5.17 (1H, d, J=10 Hz), 7.51, 7.53, 7.56 (4H), 8.16, 8.19, 8.21 (4H)

Example 38

Production of 3-O-acetyl-5-O-desosaminyl-6-O-methylerythronolide A (1) In 150 ml of tetrahydrofuran was dissolved 10 g (17.0 mmoles) of 5-O-desosaminyl-6-O-methylerythronolide A, followed by adding thereto 10.98 ml (135.6 mmoles) of pyridine, 1.04 g (8.48 mmoles) of dimethylaminopyridine and 4.82 ml (67.8 mmoles) of acetyl chloride, and the resulting mixture was stirred at room temperature for 4 days. The solvent was evaporated, followed by extraction with ethyl acetate. The extract was purified by a silica gel column chromatography (eluent; 2% methanol-chloroform) to obtain 7.82 g of 2',3-diacetyl-5-O-desosaminyl-6-O-methylerythronolide A.

$^1$H-NMR (200 MHz, CDCl$_3$) δ (ppm); 2.09 (3H, s), 2.17 (3H, s), 2.27 (6H, s)

(2) In 30 ml of methanol was dissolved 3.47 g (5.2 mmoles) of the compound obtained in (1) above, and the resulting mixture was stirred at room temperature for 2 days. The solvent was evaporated and the residue was purified by a silica gel column chromatography (eluent; 4% methanol-chloroform) to obtain 3.20 g of the title compound.

Mass (FAB) m/z; 632 [MH]$^{+1}$H-NMR (300 MHz, CDCl$_3$) δ (ppm); 2.14 (3H, s), 2.29 (6H, s), 3.05 (3H, s) IR (KBr, cm$^{-1}$); 3476, 1741, 1692

Example 39

Production of 3-O-methoxycarbonyl-5-O-desosaminyl-6-O-methylerythronolide A 9-[0-(2chlorobenzyl)oxime] 11,12-cyclic carbonate (1) 3.03 Grams (4 mmoles) of the compound obtained in Example 28, (2), 1.44 ml (12 mmoles) of trichloromethyl chloroformate, 6.46 ml (80 mmoles) of pyridine and 50 ml of dichloromethane were stirred for 5 hours in a temperature range between the freezing point to room temperature. Methanol was added and the resulting mixture was treated in the same manner as in Example 1, (4) to obtain 1.01 g of 2'-O-acetyl-5-O-desosaminyl-6-O-methylerythronolide A 9-[0-(2-chlorobenzyl)oxime] 11,12-cyclic carbonate as a white foamy substance.

(2) In 20 ml of methanol, 1 g (1.30 mmoles) of the compound obtained in (1) above was heated under reflux for 6 hours. After cooling, the crystals precipitated were collected by filtration to obtain 674 mg of the title compound as white prisms.

m.p.; 242°–243° C. (crystallized from methanol) Mass (FAB) m/z; 813 [MH]$^{+1}$H-NMR (200 MHz, CDCl$_3$) δ (ppm); 1.49 (3H, s), 2.28 (6H, s), 2.76 (3H, s), 3.80 (3H, s), 4.05 (1H, d, J=7 Hz), 4.79 (1H, s), 5.16, 5.21 (ABq, J=13 Hz), 7.14–7.35 (3H), 7.52–7.55 (1H)

Example 40

Production of 3-O-{2-[2-(2-methoxyethoxy)ethoxy]ethoxy}carbonyl-5-O-desosaminyl-6-O-methylerythronolide A In 20 ml of methylene chloride was dissolved 1.26 g (2.0 mmoles) of the compound obtained in Example 2, (1), followed by adding thereto 1.83 g (15.0 mmoles) of dimethylaminopyridine and 2.27 g (10.0 mmoles) of 2-[2-(2-methoxyethoxy)ethoxy]ethyl chloroformate at room temperature, and the resulting mixture was stirred for a day. The methylene chloride was evaporated under reduced pressure, followed by extraction with ethyl acetate. The solvent was evaporated and 2.5 g of the oily substance thus obtained was dissolved in 20 ml of methanol and allowed to stand for 2 days. The methanol was evaporated and the residue was purified by a silica gel column chromatography (eluent; 2% methanol-chloroform) to obtain 0.15 g of the title compound as colorless crystalline powder.

Mass (FAB) m/z; 780 [MH]$^{+1}$H-NMR (200 MHz, CDCl$_3$) δ (ppm); 2.30 (6H, s), 3.06 (3H, s), 3.38 (3H, s) IR (KBr, cm$^{-1}$); 3495, 1742, 1693

Example 41

Production of 3-O-(α-fluorophenyl)acetyl-5-O-desosaminyl-6-O-methylerythronolide A (1) In 10 ml of dichloromethane were dissolved 1 g of the compound obtained in Example 2, (1), 97 mg (0.79 mmole) of 4-dimethylaminopyridine and 733 mg (4.76 mmoles) of α-fluorophenylacetic acid, followed by adding thereto 909 mg (4.74 mmoles) of 1-ethyl-3-(3-dimethylaminopropyl)carbodiimide hydrochloride under ice-cooling, and the resulting mixture was stirred for 1 hour. Thereafter, 244 mg (1.58 mmoles) of α-fluorophenylacetic acid and 303 mg (1.58 mmoles) of 1-ethyl-3-(3-dimethylaminopropyl)carbodiimide hydrochloride were added and then stirred for 30 minutes. Water and ethyl acetate were added to the reaction solution to carry out extraction. The organic layer was washed successively with a saturated aqueous sodium hydrogencarbonate solution, water and a saturated aqueous sodium chloride solution and dried over anhydrous magnesium sulfate. The solvent was evaporated under reduced pressure and the residue was purified by a silica gel column chromatography (eluent; chloroform: methanol: aqueous ammonia=20:1:0.1) to obtain 0.99 g of 2'-O-acetyl-3-O-(α-fluorophenyl)acetyl-5-O-desosaminyl-6-O-methylerythronolide A.

(2) 0.99 Gram of the compound obtained in (1) above was dissolved in 10 ml of methanol and heated under reflux for 2 hours. After the reaction, the methanol was evaporated and the residue was purified by a silica gel column chromatography.(eluent; chloroform: methanol: aqueous ammonia=30:1:0.1) to obtain 0.79 g of the title compound.

Mass (FAB) m/z; 726 [MH]$^{+1}$H-NMR (300 MHz, CDCl$_3$) δ (ppm); 2.27, 2.28 (3'-N(CH$_3$)$_2$), 3.05, 3.06 (6-OCH$_3$), 7.30–7.55 (Ar-H) $^{13}$C-NMR (75 MHz, CDCl$_3$) δ (ppm); 40.3, 40.4 (3'-N(CH$_3$)$_2$), 50.0, 50.4 (6-OCH$_3$), 173.3, 173.4 (1), 220.6, 220.7 (9)

Example 42

Production of 3-O-(4-fluorophenoxy)acetyl-5-O-desosaminyl-6-O-methylerythronolide A (1) 2 Grams (3.17 mmoles) of the compound obtained in Example 2, (1) was reacted in the same manner as in Example 41, (1) except for using 194 mg (1.59 mmoles) of 4-dimethylaminopyridine, 1.6 g (9.40 mmoles) of 4-fluorophenoxyacetic acid and 1.82 g (9.50 mmoles) of 1-ethyl-3-(3-dimethylaminopropyl)carbodiimide hydrochloride, to obtain 2'-O-acetyl-3-O-(4-fluorophenoxy)-acetyl-5-O-desosaminyl-6-O-methylerythronolide A.

(2) The compound obtained in (1) above was reacted in the same manner as in Example 41, (2) to obtain 2.0 g of the title compound.

Mass (FAB)m/z; 742 [MH]$^{+1}$H-NMR (200 MHz, CDCl$_3$) δ (ppm); 2.15 (6H, s), 3.05 (3H, s), 4.62, 4.74 (2H, ABq, J=15.8 Hz), 6.89–7.03 (4H, m, Ar-H) $^{13}$C-NMR (75 MHz, CDCl$_3$) δ (ppm); 40.2 (3'-N(CH$_3$)$_2$), 50.1 (6 -OCH$_3$), 66.2 (3-OCOCH$_2$—), 116.0, 116.0, 116.2, 116.3 (Ar), 220.6 (9)

Example 43

Production of 11-amino-11-deoxy-5-O-desosaminyl-3-O-benzyloxycarbonyl-6-O-methylerythronolide A 11-N,12-O-cyclic carbamate (1) In 50 ml of acetonitrile and 5 ml of tetrahydrofuran was dissolved 5 g (5.95 mmoles) of the compound obtained in Example 12, (2), followed by adding thereto 3 ml of concentrated ammonia, and the resulting mixture was stirred at room temperature for 4 days. The solvent was evaporated under reduced pressure, after which a 2N aqueous sodium hydroxide solution and water were added to the residue, followed by extraction with ethyl acetate. The organic layer was washed with water and then a saturated aqueous sodium chloride solution and dried over anhydrous magnesium sulfate. The solvent was evaporated and the residue was purified by a silica gel column chromatography (eluent; chloroform: acetone=3:1) to obtain 1.8 g of 2'-O-acetyl-11-amino-11-deoxy-5-O-desosaminyl-3-O-benzyloxycarbonyl-6-O-methylerythronolide A 11-N,12-O-cyclic carbamate.

(2) 1.8 Grams of the compound obtained in (1) above was dissolved in 20 ml of methanol and heated under reflux for 2 hours. The reaction solution was treated in the same manner as in Example 41, (2) to obtain 0.95 g of the title compound.

Mass (FAB) m/z; 749 [MH]$^{+1}$H-NMR (200 MHz, CDCl$_3$) δ (ppm); 2.20 (6H, s), 2.98 (3H, s), 5.20 (2H, s), 7.30, 7.55 (SH, m, At-H) $^{13}$C-NMR (75 MHz, CDCl$_3$) δ (ppm); 40.3 (3'-N(CH$_3$)$_2$), 49.9 (6-OCH$_3$), 69.9 (3-OCOCH$_2$—), 217.6 (9)

Example 44

Production of 11-amino-ll-deoxy-5-O-desosaminyl-3-O-(4-nitrophenyl)acetyl-6-O-methylerythronolide A 11-N,12-O-cyclic carbamate (1) In 10 ml of methanol was dissolved 0.85 g of the compound obtained in Example 43, followed by adding thereto 170 mg of 10% palladium carbon and 358 mg (5.68 mmoles) of ammonium formate, and the reaction was carried out at room temperature for 30 minutes. The catalyst was filtered off and the solvent was evaporated under reduced pressure, after which the residue was dissolved in 6 ml of acetone, followed by adding thereto 0.15 ml (1.59 mmoles) of acetic anhydride, and the resulting mixture was stirred at room temperature for 1.5 hours. The same after-treatment as in Example 43, (1) was carried out to obtain 0.58 g of 2'-O-acetyl-11-amino-11-deoxy-5-O-desosaminyl-6-O-methylerythronolide A 11-N,12-O-cyclic carbamate.

(2) In 1 ml of dichloromethane were dissolved 240 mg (1.32 mmoles) of 4-nitrophenylacetic acid, 0.18 ml (1.29 mmoles) of triethylamine and 0.16 ml (1.30 mmoles) of pivaloyl chloride, and the resulting solution was stirred at −15° C. for 15 minutes. A solution of 0.29 g of the compound obtained in (1) above in 2 ml of dichloromethane was added dropwise thereto at room temperature. After stirring for 1.5 hours, the reaction mixture was extracted with dichloromethane. The solvent was evaporated under reduced pressure and the residue was reacted in the same manner as in Example 41, (2). The reaction product was crystallized from ethyl acetate-hexane to obtain 0.22 g of the title compound.

Mass (FAB) m/z; 778 [MH]$^+$

Example 45

Production of 3-O-(N-t-butoxycarbonyl)glycyl-5-O-desosaminyl-6-O-methylerythronolide A (1) In 10 ml of dichloromethane were dissolved 1 g (1.58 mmoles) of the compound obtained in Example 2, (1), followed by adding thereto 553 mg (3.16 mmoles) of N-t-butoxycarbonylglycine, 97 mg (0.79 mmole) of 4-dimethylaminopyridine and 606 mg (3.16 mmoles) of 1-ethyl-3-(3-dimethylaminopropyl)carbonylimide hydrochloride, and the reaction was carried out at room temperature for 2 days. 276 Milligrams (1.58 mmoles) of N-t-butoxycarbonylglycine and 303 mg (1.58 mmoles) of 1-ethyl-3-(3-dimethylaminopropyl)carbonylimide hydrochloride were added and stirred for another 1.5 hours. After-treatment was carried out in the same manner as in Example 41, (1) and the residue was crystallized from ethyl acetate-hexane to obtain 0.77 g of 2'-O-acetyl-3-O-(N-t-butoxycarbonyl)glycyl-5-O-desosaminyl-6-O-methylerythronolide A.

(2) 0.8 Gram of the compound obtained in (1) above was reacted in the same manner as in Example 41, (2) to obtain 0.39 g of the title compound.

Mass (FAB) m/z; 747 [MH]$^{+1}$H-NMR (300 MHz, CDCl$_3$) δ (ppm); 1.43 (9H, s), 2.26 (6H, s), 3.04 (3H, s) $^{13}$C-NMR (75 MHz, CDCl$_3$) δ (ppm); 28.3 (t-Bu), 40.3 (3'-N(CH$_3$)$_2$), 50.1 (6-OCH$_3$), 220.7 (9)

Example 46

Production of 3-O-(N-benzyloxycarbonyl)glycyl-5-O-desosaminyl-6-O-methylerythronolide A Reaction was carried out in the same manner as in Example 45, (1) and (2) except for using 2 g of the compound obtained in Example 2, (1), 1.99 g (9.52 moles) of N-benzyloxycarbonylglycyl, 194 mg (1.59 mmoles) of 4-dimethylaminopyridine and 1.82 g (9.49 mmoles) of 1-ethyl-3-(3-dimethylaminopropyl)carbodiimide hydrochloride, to obtain 2.4 g of the title compound.

Mass (FAB) m/z; 781 [MH]$^{+1}$H-NMR (300 MHz, CDCl$_3$) δ (ppm); 2.25 (6H, s, 3'-N(CH$_3$)$_2$), 3.03 (3H, s, 6-OCH$_3$), 5.47 (1H, m, —NHCOO—), 7.30–7.41 (5H, m, Ar-H) $^{13}$C-NMR (75 MHz, CDCl$_3$) δ (ppm); 40.3 (3'-N(CH$_3$)$_2$), 50.0 (6-OCH$_3$), 67.1 (—COOCH$_2$Ph), 173.5 (1), 220.7 (9)

Example 47

Production of 3-0-glycyl-5-O-desosaminyl-6-O-methylerythronolide A

In 20 ml of methanol was dissolved 2.0 g (2.56 mmoles) of the compound obtained in Example 46, followed by adding thereto 0.4 g of 10% palladium carbon and 1.6 g (25.4 moles) of ammonium formate, and the resulting mixture was stirred at room temperature for 1.5 hours. The catalyst was filtered off and the filtrate was evaporated under reduced pressure. The residue was crystallized from ethyl acetate-hexane to obtain 0.95 g of the title compound.

Mass (FAB) m/z; 647 [MH]$^{+1}$H-NMR (300 MHz, CDCl$_3$) δ (ppm); 2.25 (6H, s, 3'-N(CH$_3$)$_2$), 3.05 (3H, s, 6-OCH$_3$), 3.52 (2H, m, 3-OCOCH$_2$NH$_2$), $^{13}$C-NMR (75 MHz, CDCl$_3$) δ (ppm); 40.4 (3'-N(CH$_3$)$_2$), 44.3 (3-OCOCH$_2$), 50.1 (6-OCH$_3$), 220.7 (9)

Example 48

Production of (3R)-3-O-(4-nitrophenyl)acetyl-5-O-desosaminyl-6-O-methylerythronolide A 9-oxime 11,12cyclic carbonate (1) To 50 ml of a solution of 2.44 ml (28.0 mmoles) of oxalyl chloride in dichloromethane which had been cooled to −70° C. was added dropwise 5 ml of a solution of 2.68 ml (37.6 mmoles) of dimethyl sulfoxide in dichloromethane, and the resulting mixture was stirred as it was for 10 minutes. Then, 40 ml of a solution in dichloromethane of 10 g (14.0 mmoles) of the compound obtained in production process (I), (4) in Example 1 was added dropwise over a period of about 50 minutes and stirred at −70° C. for 10 minutes and then at −55° C. for 15 minutes. To the reaction solution was added 14 ml of triethylamine, and the resulting mixture was stirred at 0° C. for 10 minutes, after which a saturated aqueous sodium chloride solution was added to carry out extraction. The organic layer was washed once more with a saturated aqueous sodium chloride solution and then dried over anhydrous magnesium sulfate. The solvent was evaporated under reduced pressure and the residue was purified by a silica gel column chromatography (eluent; chloroform: methanol: aqueous ammonia=30:1:01) to obtain 8.3 g of 3-deoxy-3-oxo-5-O-desosaminyl-6-O-methylerythronolide A 9-oxime 11,12-cyclic carbonate.

m.p.; 204°–206° C. (recrystallized from ethyl acetate-n-hexane) Mass (FAB) m/z; 629 [MH]$^{+1}$H-NMR (300 MHz, CDCl$_3$) δ (ppm); 1.01 (3H, d, J=8 Hz), 1.37 (3H, d, J=8 Hz), 1.54 (3H, s), 2.27 (6H, s), 2.70 (3H, s), 4.21 (1H, d, J=7 Hz), 4.30 (1H, d, J=9 Hz), 4.80 (1H, s), 5.05 (1H, dd, J=12 Hz, 2Hz), 7.82 (1H, broad-s) $^{13}$C-NMR (75 MHz, CDCl$_3$) δ (ppm); 49.8 (q), 78.5 (s), 84.5 (s), 103.8 (d), 154.0 (s), 165.0 (s), 169.1 (s), 203.8 (s) IR (KBr, cm$^{-1}$); 3539, 1810, 1745, 1713, 1048

(2) In 60 ml of methanol was dissolved 6.2 g (9.87 mmoles) of the compound obtained by the method described in (1) above, followed by adding thereto 995 mg (26.3 mmoles) of 90% sodium borohydride, and the reaction was carried out at room temperature for 8 hours. A conventional after-treatment was carried out to obtain 3.8 g of (3R)-5-O-desosaminyl-6-O-methylerythronolide A 9-oxime 11,12-cyclic carbonate.

(3) In 40 ml of dichloromethane was dissolved 3.8 g of the compound obtained in (2) above, followed by adding thereto 2.5 g (29.8 mmoles) of sodium hydrogen-carbonate and 1.4 ml (14.8 mmoles) of acetic anhydride, and the resulting mixture was stirred at room temperature for 3 hours. A conventional after-treatment was carried out to obtain 3.9 g of (3R)-2'-O-acetyl-5-O-desosaminyl-6-O-methylerythronolide A 9-acetoxime 11,12-cyclic carbonate.

(4) In 10 ml of dichloromethane was dissolved 3.0 g of the compound obtained in (3) above. The solution was added to a solution of 2.3 g (12.7 mmoles) of 4-nitrophenylacetic acid, 1.76 ml (12.6 mmoles) of triethylamine and 1.55 ml (12.6 mmoles) of pivaloyl chloride in 20 ml of dichloromethane at −15° C. and stirred at room temperature for 4 days. A conventional after-treatment was carried out and the residue was purified by a silica gel column chromatography (eluent; chloroform: acetone=2:1) to obtain 1.2 g of (3R)-2'-O-acetyl-3-O-(4-nitrophenyl)acetyl-5-O-desosaminyl-6-O-methylerythronolide A 9-acetoxime 11,12-cyclic carbonate.

(5) 1.2 Grams of the compound obtained in (4) above was reacted in the same manner as in Example 41, (2) to obtain 0.65 g of the title compound.

$^1$H-NMR (300 MHz, CDCl$_3$) δ (ppm); 2.31 (6H, s), 3.02 (3H, s), 3.73, 3.87 (2H, ABq), 8.33 (1H, broad-s) $^{13}$C-NMR (75 MHz, CDCl$_3$) δ (ppm); 40.3 (3'-N(CH$_3$)$_2$), 49.7 (6-OCH$_3$), 123.8, 130.5

Example 49

Production of 3-O-(3-nitrophenyl)acetyl-5-O-desosaminyl-6-O-methylerythronolide A 1.26 Grams (2 mmoles) of the compound obtained in Example 2, (1) and 1.087 g (6 mmoles) of 3-nitrophenylacetic acid were reacted in the same manner as in Example 1, (5) to obtain 970 mg of the title compound as a light-yellow foamy substance.

$^1$H-NMR (200 MHz, CDCl$_3$) δ (ppm); 2.39 (6H, s), 3.02 (3H, s), 7.50, 7.53, 7.58 (1H, Ar-H), 7.69, 7.71 (1H, Ar-H), 8.15–8.22 (2H, Ar-H)

Example 50

Production of 3-O-(4-nitrophenyl)acetyl-5-O-desosaminylerythronolide B (1) 50 Grams of erythromycin B was reacted in the same manner as in Example 1, (1) to obtain 30.62 g of 5-O-desosaminylerythronolide B.

(2) 6.84 Grams of the compound obtained in (1) above was acetylated in the same manner as in Example 2, (1) to obtain 6.30 g of 2'-O-acetyl-5-O-desosaminylerythronolide B as a white foamy substance.

(3) 1.23 Grams (2 mmoles) of the compound obtained in (2) above and 1.087 g (6 mmoles) of 4-nitrophenylacetic acid were reacted in the same manner as in Example 1, (5) to obtain 780 mg of the title compound as light-brown powder.

Mass (FAB)m/z; 723 [MH]$^{+1}$H-NMR (200 MHz, CDCl$_3$) δ (ppm); 2.26 (6H, s), 3.36 (1H, broad-s), 3.81, 3.82 (2H, ABq), 3.99 (1H, d), 7.51, 7.55 (2H, Ar-H), 8.17, 8.23 (2H, Ar-H) $^{13}$C-NMR (75 MHz, CDCl$_3$) δ (ppm); 40.3 (3'-NMe$_2$), 75.2 (6), 123.7, 130.5, 141.1, 147.3 (Ar-C), 220.1 (9) IR (KBr, cm$^{-1}$); 3460, 1737, 1524, 1348, 1170

Example 51

Production of 2'-O-nicotinoyl-3-O-(4-nitrophenyl)acetyl-5-O-desosaminyl-6-O-methylerythronolide A 11,12-cyclic carbonate In 20 ml of acetone was dissolved 1.506 g (2 moles) of the compound of Example 4, followed by adding thereto 712 mg (4 mmoles) of nicotnoyl chloride hydrochloride and 840 mg (10 mmoles) of sodium hydrogen-carbonate, and the resulting mixture was stirred at room temperature for 22 hours. In 30 ml of dichloromethane was dissolved 2.78 g of an ethyl acetate extract of the mixture, and conversion to 11,12-cyclic carbonate was carried out under ice-cooling in the same manner as in Example 1, (4) except for using 3.23 ml of pyridine and 0.6 ml of trichloromethyl chloroformate, to obtain 1.58 g of the title compound as a light-yellow foamy substance.

$^1$H-NMR (200 MHz, CDCl$_3$) δ (ppm); 2.26 (6H, s), 2.98 (3H, s), 4.66 (1H, s), 4.93 (1H, dd), 7.42–7.49 (1H, Ar-H), 7.57, 7.62 (2H, Ar-H), 8.25, 8.29 (2H, Ar-H), 8.81–8.84 (1H, Ar-H), 9.21, 9.22 (1H, Ar-H)

Example 52

Production of 3-O-phenylalanyl-5-O-desosaminyl-6-O-methylerythronolide A (1) 5 Grams (7.92 mmoles) of the compound obtained in Example 2, (1), 7.11 g (23.76 mmoles) of (N-benzyloxycarbonyl)phenylalanine, 1.16 g (9.504 mmoles) of 4-dimethylaminopyridine, 3.29 ml (23.76 mmoles) of triethylamine and 2.93 ml (23.76 mmoles) of pivaloyl chloride were stirred in 100 ml of dichloromethane at room temperature for 3 days. After-treatment and deacetylation were carried out in the same manner as in Example 1, (5) to obtain 120 mg of 3-O-(N-benzyloxy-carbonyl)phenylalanyl-5-O-desosaminyl-6-O-methylerythronolide A as a white foamy substance.

(2) To methanol were added a drop of 65 mg (0.07 mmole) of the compound obtained in (1) above, 30 mg of 5% palladium carbon, 47 mg (0.7 mmole) of ammonium formate and one drop of formic acid, and the reaction was carried out in the same manner as in Example 48 to obtain 35 mg of the title compound as a white foamy substance.

Mass (FAB) m/z; 737 [MH]$^+$ $^1$H-NMR (200 MHz, CDCl$_3$) δ (ppm); 2.28 (6H, s), 3.06 (3H, s), 7.13–7.37 (5H, Ar-H)

Example 53

Production of 3-O-(2,4-dichlorophenyl)acetyl-5-O-desosaminyl-6-O-methylerythronolide A 1.26 Grams (2 mmoles) of the compound obtained in Example 2, (1) and 1.23 g (6 mmoles) of 2,4-dichlorophenylacetic acid were reacted in the same manner as in Example 1, (5) to obtain 750 mg of the title compound as a white foamy substance.

$^1$H-NMR (200 MHz, CDCl$_3$) δ (ppm); 2.31 (6H, s), 3.04 (3H, s), 7.21–7.35 (2H, Ar-H), 7.43, 7.44 (1H, Ar-H)

Example 54

Production of 3-O-(4-nitrophenoxy)acetyl-5-O-desosaminyl-6-O-methylerythronolide A In 30 ml of dichloromethane was dissolved 1.26 g (2 mmoles) of the compound obtained in Example 2, (1), followed by adding thereto 1.183 g (6 mmoles) of 4-nitrophenoxyacetic acid, 1.15 g (6 mmoles) of 1-ethyl-3-(3-dimethylaminopropyl)carbodiimide hydrochloride and 244 mg (2 mmoles) of 4-dimethylaminopyridine, and the reaction was carried out for 22 hours. Then, after-treatment was carried out in the same manner as in Example 18, (1). Subsequently, deprotection was conducted by heating in methanol to obtain 530 mg of the title compound as a light-yellow foamy substance.

$^1$H-NMR (200 MHz, CDCl$_3$) δ (ppm); 2.17 (6H, s), 3.05 (3H, s), 4.79, 4.87 (2H, ABq), 7.00, 7.04 (2H, At-H), 8.22, 8.26 (2H, Ar-H)

Example 55

Production of 3-O-(4-methylphenyl)acetyl-5-O-desosaminyl-6-O-methylerythronolide A 1.26 Grams (2 mmoles) of the compound obtained in Example 2, (1) and 901 mg (6 mmoles) of 4-methylphenylacetic acid were reacted in the same manner as in Example 1, (5) to obtain 96 mg of the title compound as a white foamy substance.

$^1$H-NMR (200 MHz., CDCl$_3$) δ (ppm); 2.29 (6H, s), 2.32 (3H, s), 3.04 (3H, s), 7.11, 7.15, 7.22, 7.27 (4H, Ar-H)

Example 56

Production of 3-O-(2-nitrophenyl)acetyl-5-O-desosaminyl-6-O-methylerythronolide A 1.26 Grams (2 mmoles) of the compound obtained in Example 2, (1) and 1.087 g (6 mmoles) of 2-nitrophenylacetic acid were reacted in the same manner as in Example 1, (5) to obtain 610 mg of the title compound as a light-yellow foamy substance.

$^1$H-NMR (200 MHz, CDCl$_3$) δ (ppm); 2.30 (6H, s), 3.01 (3H, s), 7.35–7.64 (3H, Ar-H), 8.07, 8.11 (1H, Ar-H)

Example 57

Production of 3-O-(2-chlorophenyl)acetyl-5-O-desosaminyl-6-O-methylerythronolide A Using 1.26 g (2 mmoles) of the compound obtained in Example 2, (1) and 1.02 g (6 mmoles) of 2-chlorophenylacetic acid, 0.98 g of the title compound was obtained as crystalline powder by reacting them in the same manner as in Example 1, (5).

m.p.; 185°–187° C. (recrystallized from ethyl acetate-hexane) Mass (FAB) m/z; 742 [MH]$^{+1}$H-NMR (300 MHz, CDCl$_3$) δ (ppm); 2.29 (6H, s), 3.04 (3H, s), 3.85, 3.92 (2H, ABq, J=17 Hz), 7.20–7.28 (2H, m, Ar-H), 7.33–7.43 (2H, m, Ar-H)) IR (KBr, cm$^{-1}$); 3534, 1736, 1703

Example 58

Production of 3-O-(3-chlorophenyl)acetyl-5-O-desosaminyl-6-O-methylerythronolide A Using 1.26 g (2 mmoles) of the compound obtained in Example 2, (1) and 1.02 g (6 mmoles) of 3-chlorophenylacetic acid, 0.93 g of the title compound was obtained as crystalline powder by reacting them in the same manner as in Example 1, (5).

m.p.; 167°–169° C. (recrystallized from acetone-hexane) Mass (FAB) m/z; 742 [M/t]$^{+1}$H-NMR (300 MHz, CDCl$_3$) δ (ppm); 2.27 (6H, s), 3.04 (3H, s), 3.65, 3.72 (2H, ABq, J=15 Hz), 7.22–7.31 (3H, m, Ar-H), 7.34–7.37 (1H, m, Ar-H)) IR (KBr, cm$^{-1}$); 3536, 1736, 1698, 1599, 1576

Example 59

Production of 3-O-(3,4,5-trimethoxyphenyl)-acetyl-5-O-desosaminyl-6-O-methylerythronolide A Using 1.26 g (2 mmoles) of the compound obtained in Example 2, (1) and 1.35 g (6 mmoles) of 3,4,5-trimethoxyphenylacetic acid, 0.77 g of the title compound was obtained as a light-yellow foamy substance by reacting them in the same manner as in Example 1, (5).

Mass (FAB) m/z; 798 [MH]$^{+1}$H-NMR (300 MHz, CDCl$_3$) δ (ppm); 2.26 (6H, s), 3.06 (3H, s), 3.59, 3.65 (2H, ABq, J=15 Hz), 3.82 (3H, s), 3.85 (6H, s), 6.60 (2H, s, Ar-H) IR (KBr, cm$^{-1}$); 3474, 1741, 1693, 1592

Example 60

Production of 3-O-(3,4,5-trimethoxyphenyl)-acetyl-5-O-desosaminyl-6-O-methylerythronolide A 11,12cyclic carbonate (1) In 1 liter of dichloromethane was dissolved 500 g (0.668 mole) of 6-O-methylerythromycin A, followed by adding thereto 220.8 ml (2.34 moles) of acetic anhydride and 32.67 g (0.267 mole) of 4-dimethylaminopyridine, and the resulting mixture was stirred at room temperature for 2 days. The reaction solution was washed with a dilute sodium hydroxide solution and then dried over anhydrous magnesium sulfate. The solvent was evaporated and the crude crystals thus obtained were crystallized from ethyl acetate to obtain 485.2 g of 2',4"-di-O-acetyl-6-O-methylerythromycin A.

(2) In 100 ml of dichloromethane was dissolved 14.38 g (17.3 mmoles) of the compound obtained in (1) above, and 12.6 ml (1.56 mmoles) of pyridine was added under ice-cooling, after which a solution of 3.1 ml (25.9 mmoles) of trichloro chloroformate in 10 ml of dichloromethane was added dropwise over a period of 10 minutes. The reaction mixture was extracted with dichloromethane and the yellow crude crystals thus obtained were crystallized from ethyl acetate to obtain 13.3 g of 2',4"-di-O-acetyl-6-O-methylerythromycin A 11,12-cyclic carbonate.

m.p.; 242°–244° C. Mass (FAB) m/z; 858 [MH]$^+$ $^1$H-NMR (300 MHz, CDCl$_3$) δ (ppm); 2.05 (3H, s), 2.11 (3H, s), 2.28 (6H, s), 2.97 (3H, s), 3.35 (3H, s) IR (KBr, cm$^{-1}$); 3459, 1817, 1742, 1720

(3) The compound obtained in (2) above was treated in the same manner as in production process (I), (1) in Example 1 to obtain 2'-O-acetyl-5-O-desosaminyl-6-O-methylerythronolide A.

(4) Using 0.66 g (1 mmole) of the compound obtained in (3) above and 0.68 g (3 soles) of 3,4,5-trimethoxyphenylacetic acid, 0.24 g of the title compound was obtained by reacting them in the same manner as in Example 1, (5).

Mass(FAB) m/z; 824 [MH]$^+$

Example 61

Production of 11-amino-11-deoxy-3-O-(3,4,5-trimethoxyphenyl)acetyl-5-O-desosaminyl-6-O-methylerythronolide A 11-N,12-O-cyclic carbamate (1) In a mixed solution of 225 ml of N,N-dimethylformamide and 375 ml of tetrahydrofuran was dissolved 150 g (0.18 mole) of the compound obtained in Example 60, (2), i.e., 2',4"-di-O-acetyl-6-O-methylerythromycin A 11,12-cyclic carbonate, followed by adding thereto 73.08 g (0.45 mole) of 1,1'-carbonyldiimidazole. Under ice-cooling, 9.37 g (0.23 mole) of 60% sodium hydride was added at 5 to 7° C. and stirred for 1 hour. The resulting mixture was brought back to room temperature and subjected to reaction for 2.5 hours. The reaction mixture was extracted with ethyl acetate to obtain 200.79 g of colorless and foamy 10, 11-anhydro-2',4"-O-acetyl-12-O-imidazolylcarbonyl-6-O-methylerythromycin A.

(2) A solution of the compound obtained in (1) above, in 400 ml of tetrahydrofuran was added dropwise to a mixed solution of 500 ml of liquid ammonia and 200 ml of tetrahydrofuran under cooling with dry ice and acetone, and the resulting mixture was stirred at room temperature for 2 days. Then, 2.16 g (0.054 mole) of 60% sodium hydride was added and the reaction was carried out for 3 hours. The reaction mixture was extracted with ethyl acetate to obtain 174.35 g of 11-amino-11-deoxy-2',4"-di-O-acetyl-6-O-methylerythronolide A 11-N,12-O-cyclic carbamate as colorless crystalline powder.

m.p.; 249°–251° C. (crystallized from acetonitrile) Mass (FAB) m/z; 857 [MH]$^+$IR (KBr, cm$^{-1}$); 3442, 1779, 1742, 1703

(3) 174.35 Grams obtained in (2) above was treated in the same manner as in production process (I), (1) in Example 1 to obtain 116.2 g of 2'-O-acetyl-11-amino-11-deoxy-5-O-desosaminyl-6-O-methylerythronolide A 11-N,12-O-cyclic carbamate.

m.p.; 168°–170° C., 247°–249° C. (recrystallized from acetone-hexane)

(4) Using 1.97 g (3 mmoles) of the compound obtained in (3) above and 2.04 g (9 mmoles) of 3,4,5-trimethoxyphenylacetic acid, 0.88 g of the title compound was obtained as colorless crystalline powder by reacting them in the same manner as in Example 1, (5).

m.p.; 184°–186° C. (recrystallized from acetone-hexane)
Mass (FAB) m/z; 823 [MH]$^{+1}$H-NMR (300 MHz, CDCl$_3$) δ (ppm); 2.25 (6H, s), 2.98 (3H, s), 3.60, 3.66 (2H, ABq, J=15 Hz), 3.83 (3H, s), 3.85 (6H, s), 5.78 (1H, bs), 6.58 (2H, s, Ar-H)

IR (KBr, cm$^{-1}$); 3431, 1771, 1746, 1703, 1592

Example 62

Production of 3-O-(4-nitrophenyl)acetyl-5-O-desosaminylerythronolide A 9-{O-[2-(N-benzyl-N-methyamino)ethyl]oxime}

(1) In 40 ml of methanol was dissolved 4.4 g (6.84 mmoles) of 5-O-desosaminylerythronolide A 9-[O-(2-aminoethyl) oxime] obtained in the same manner as in Example 31, (1), followed by adding thereto 0.98 ml (17.12 mmoles) of acetic acid, 0.7 ml (6.89 mmoles) of benzaldehyde and 0.645 g (10.26 mmoles) of sodium cyanoborate, and the resulting mixture was stirred as it was for 1.5 hours. The methanol was evaporated under reduced pressure and a 2N sodium hydroxide solution was added to the residue, followed by extraction with ethyl acetate. The organic layer was washed with water and then a saturated aqueous sodium chloride solution and dried over anhydrous magnesium sulfate. The solvent was evaporated under reduced pressure, after which the residue was purified by a silica gel column chromatography to obtain 1.74 g of 5-O-desosaminylerythronolide A 9-{O-[(2-benzylamino)ethyl]oxime}.

(2) In 15 ml of ethanol was dissolved 1.74 g (2.37 mmoles) of the compound obtained in (1) above, followed by adding thereto 0.87 ml (10.98 mmoles) of a 35% formaldehyde solution and 0.33 ml (7.75 mmoles) of 90% formic acid, and the resulting mixture was refluxed for 2.5 hours. After-treatment was carried out in the same manner as in (1) above to obtain 1.5 g of a clude product. The clude product was acetylated at the 2'-position in the same manner as in Example 2, (1) to obtain 1.2 g of 2'-0-acetyl-5-O-desosaminylerythronolide A 9-{O-[2-(N-benzyl-N-methylamino)ethyl]oxime}.

(3) 3 Milliliters of a solution in dichloromethane of 0.413 g (2.28 mmoles) of 4-nitrophenylacetic acid, 0.32 ml (2.30 mmoles) of triethylamine and 0.28 ml (2.27 mmoles) of pivaloyl chloride was stirred at −15° C. for 20 minutes. To this solution was added dropwise a solution (3 ml) in dichloromethane of 0.6 g (0.76 mmole) of the compound obtained in (2) above, at room temperature. Then, stirring was continued for 1.5 hours and after-treatment was carried out in the same manner as in (1) above. The solvent was evaporated, after which the residue was subjected to deacetylation in the same manner as in Example 21, (2). The methanol was evaporated and the resulting residue was purified by a silica gel column chromatography to obtain 0.60 g of the title compound.

Mass (FAB) m/z; 901 [MH]$^{+1}$H-NMR (300 MHz, CDCl$_3$) δ (ppm); 2.31 (6H, s), 7.23–7.38, 7.51–7.58, 8.17–8.24 (9H, m)

Example 63

Production of 3-O-[2-(4-nitrophenyl)propionyl]-5-O-desosaminyl-6-O-methylerythronolide A Using 1.0 g (1.58 mmoles) of the compound obtained in Example 2, (1) and 0.928 g (4.75 mmoles) of 2-(4-nitrophenyl)propionic acid, 0.27 g of the title compound was obtained as crystals by reacting them in the same manner as in Example 21, (1) and (2), followed by crystallization from ethyl acetate.

Mass (FAB) m/z; 767 [MH]$^{+1}$H-NMR (300 MHz, CDCl$_3$) δ (ppm); 1.64 (3H, d), 2.26 (6H, s), 3.04 (3H, s), 7.63–7.71, 8.20–8.29 (4H, m, Ar-H) $^{13}$C-NMR (75 MHz, CDCl$_3$) δ (ppm); 40.0 (3'-N(CH$_3$)$_2$), 50.2 (6-OCH$_3$), 123.7, 129.2 (Ar), 220.7 (9)

Example 64

Production of 3-O-[2-(4-nitrophenyl)propionyl]-5-O-desosaminyl-6-O-methylerythronolide A 11,12-cyclic carbonate Using 1.92 g (2.51 mmoles) of the compound obtained in Example 63, 0.96 g of the title compound was obtained by reacting the former compound in the same manner as in Example 1, (4).

Mass (FAB) m/z; 793 [MH]$^{+1}$H-NMR (300 MHz, CDCl$_3$) δ (ppm); 2.23, 2.29 (3'-N(CH$_3$)$_2$), 2.98 (6-OCH$_3$), 7.48–7.55, 7.60–7.66, 8.16–8.26 (Ar-H) $^{13}$C-NMR (75 MHz, CDCl$_3$) δ (ppm); 40.2, 40.3 (3'-N(CH$_3$)$_2$), 49.8, 49.9 (6-OCH$_3$), 123.7, 123.9, 128.8, 129.2 (Ar), 212.0, 121.2 (9)

Example 65

Production of 3-O-mandelyl-5-O-desosaminyl-6-O-methylerythronolide A

Using 1.0 g (1.58 mmoles) of the compound obtained in Example 2, (1) and 0.92 g (4.74 mmoles) of O-acetylmandelic acid, 1.17 g of a mixture of epimers due to the substituent at the 3-position was obtained as crystals by reacting them in the same manner as in Example 21, (1) and (2).

The mixture obtained was purified by a silica gel column chromatography to obtain epimer (A) (0.08 g) and epimer B (0.24 g).

Epimer A

Mass (FAB) m/z; 724 [MH]$^{+1}$H-NMR (300 MHz, CDCl$_3$) δ (ppm); 2.31 (6H, s), 3.05 (3H, s), 7.30–7.48 (5H, m) $^{13}$C-NMR (75 MHz, CDCl$_3$) δ (ppm); 40.2 (3'-N(CH$_3$)$_2$), 50.0 (6-OCH$_3$), 126.6, 128.6, 128.7 (Ar), 220.7 (9)

Epimer B

Mass (FAB) m/z; 724 [MH]$^{+1}$H-NMR (300 MHz, CDCl$_3$) δ (ppm); 2.30 (6H, s), 3.04 (3H, s), 7.28–7.58 (5H, m) $^{13}$C-NMR (75 MHz, CDCl$_3$) δ (ppm); 40.1 (3'-N(CH$_3$)$_2$), 50.1 (6-OCH$_3$), 126.1, 128.4, 128.6 (Ar), 220.7 (9)

Example 66

Production of 3-O-phenylglycylglyci-5-O-desosaminyl-6-O-methylerythronolide A and 3-O-(2,4-dioxoperhydropyrimidin-3-yl)acetyl-5-O-desosaminyl-6-O-methylerythronolide A (1) Using 20 g (31.70 mmoles) of the compound obtained in Example 2, (1) and 19.9 g (95.2 mmoles) of N-benzyloxycarbonylglycine, 26 g of 2'-O-acetyl-3-O-(N-benzyloxycarbonyl)glycyl-5-O-desosaminyl-6-O-methylerythronolide A was obtained by reacting them in the same manner as in Example 21, (1).

(2) In 200 ml of ethanol was dissolved 26 g (31.63 mmoles) of the compound obtained in (1) above, followed by adding thereto 2.5 g of 10% palladium carbon and 13.5 ml (316.95 mmoles) of 90% formic acid, and stirring was continued at room temperature for 2 hours. After the catalyst was filtered off, the same after-treatment as in Example 61, (1) was carried out. The solvent was evaporated under reduced pressure to obtain 18.9 g of 2'-O-acetyl-3-O-glycyl-5-O-desosaminyl-6-O-methylerythronolide A.

(3) In 30 ml of tetrahydrofuran was dissolved 3 g (4.36 mmoles) of the compound obtained in (2) above, followed by adding thereto 1.37 g (4.80 mmoles) of N-benzyloxycarbonylphenylglycine, 0.6 g (5.21 mmoles) of N-hydroxysuccinimide and 1.0 g (5.22 mmoles) of 1-ethyl-3-(3-dimethylaminopropyl)carbodiimide hydrochloride, and the resulting mixture was stirred at room temperature for 3 hours. After the reaction, water was added to the reaction solution, followed by extraction with ethyl acetate. The organic layer was washed with water and then a saturated aqueous sodium chloride solution and dried over anhydrous magnesium sulfate. The solvent was evaporated under reduced pressure, after which deacetylation at the 2'-position was carried out in the same manner as in Example 21, (2). The reaction solution was concentrated and the residue was purified by a silica gel column chromatography to obtain 0.74 g of 3-O-(2,4-dioxo-perhydropyrimidin-3-yl) acetyl-5-O-desosaminyl-6-O-methylerythronolide A.

Mass (FAB) m/z; 744 [MH]$^{+1}$H-NMR (300 MHz, CDCl$_3$) δ (ppm); 2.74 (6H, s), 3.04 (3H, s), 4.55, 4.76 (2H, ABq) $^{13}$C-NMR (75 MHz, CDCl$_3$) δ (ppm); 39.1 (3'-N(CH$_3$)$_2$), 41.3 (3-OCOCH$_2$—), 50.2 (6-OCH$_3$), 220.6 (9)

2.62 Grams of 3-0-(N-benzyloxycarbonyl) phenylglycylglyci-5-O-desosaminyl-6-O-methylerythronolide A was also obtained.

(4) In 10 ml of methanol was dissolved 1.0 g (1.10 mmoles) of the 3-0-(N-benzyloxycarbonyl)phenylglycylglyci-5-O-desosaminyl-6-O-methylerythronolide A, followed by adding thereto 40 mg of 10% palladium carbon and 0.69 g (10.95 mmoles) of ammonium formate, a stirring was continued overnight at room temperature. After the reaction, the catalyst was filtered off, followed by concentration and purification by a silica gel column chromatography, whereby 0.272 g of 3-O-phenylglycylglyci-5-O-desosaminyl-6-O-methylerythronolide A was obtained.

Mass (FAB) m/z; 780 [MH]$^{+1}$H-NMR (300 MHz, CDCl$_3$) δ (ppm); 2.23 (6H, s), 3.05 (3H, s), 7.26–7.43 (5H, m) $^{13}$C-NMR (75 MHz, CDCl$_3$) δ (ppm); 40.3 (3'-N(CH$_3$)$_2$), 50.1 (6-OCH$_3$), 126.9, 128.2, 128.9, 140.6 (Ar), 169.8 (—NHCO—), 220.7 (9)

Test Example (in vitro antibacterial activity)

The in vitro antibacterial activity of the compounds of the present invention against various test bacteria was determined according to the MIC measuring method of Japanese Chemotherapeutic Association by using a sensitive disc media (available from Eiken Chemical Co.). The results are expressed in MIC values (minimum inhibitory concentration mcg/ml) and shown in Table 1 and Table 2. 6-O-methylerythromycin A was used as a reference agent in Table 1, and erythromycin A in Table 2.

TABLE 1 in vitro Antibacterial activity MIC value (mcg/ml)

| Micro-organism | Compound | | | |
| --- | --- | --- | --- | --- |
| | Example 1 | Example 3 | Example 9 | Reference agent |
| S. aureus 209P-JC | 0.025 | 0.05 | 0.025 | 0.05 |
| S. aureus Smith 4 | 0.05 | 0.10 | 0.05 | 0.10 |
| S. epidermides IID 866 | 0.05 | 0.10 | 0.05 | 0.10 |
| E. faecalis CSJ 1212 | 0.05 | 0.10 | 0.05 | 0.78 |
| S. aureus J-109 | >100 | >100 | >100 | >100 |
| S. aureus B1 | 0.10 | 0.20 | 0.20 | >100 |
| S. aureus C1 | 0.10 | 0.10 | 0.05 | 25 |

TABLE 2 in vitro Antibacterial activity MIC value (mcg/ml)

| Micro-organism | Compound | |
| --- | --- | --- |
| | Example 15 | Reference agent |
| S. aureus 209P-JC | 0.05 | 0.10 |
| S. aureus Smith 4 | 0.05 | 0.20 |
| S. epidermides IID 866 | 0.05 | 0.10 |
| E. faecalis CSJ 1212 | 0.05 | 0.78 |
| S. aureus J-109 | >100 | >100 |
| S. aureus B1 | 0.10 | >100 |
| S. aureus C1 | 0.78 | >100 |

We claim:
1. A 5-0-desosaminylerythronolide derivative represented by the formula:

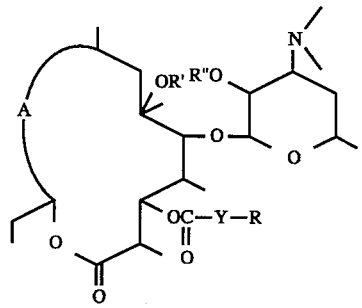

wherein:

Y is a group represented by the formula:

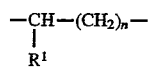

(wherein R$^1$ is a hydrogen atom, a hydroxyl group, a halogen atom, a C$_1$–C$_3$ alkyl group or an amino group, and n is an integer of 0 to 4), an oxygen atom, a vinylene group, or a group represented by the formula —CH$_2$—NH—CO, R is a C$_7$–C$_{15}$ aralkyl group; a C$_7$–C$_{15}$ aralkyl group substituted by at least one member selected from the group consisting of a nitro group, a methoxy group, a methoxythio group, a methoxycarbonyl group, a carboxy group, a methylene group, a halogen atom, a trifluoromethyl group, an amino group and a demethylamino group; a phenyl group; a phenyl group having 1 to 5 substituents selected from the group consisting of halogen atoms, nitro groups, amino groups, C$_1$–C$_3$ alkyl groups, C$_1$–C$_3$ alkyl groups substituted by one or more halogen atoms, C$_1$–C$_4$ alkylamino groups, C$_2$–C$_7$ acylamino groups and $C_1-C_4$ alkoxy groups; a naphthyl group; a thiazolyl group; an imidazolyl group; an amino-thiazolyl group; a biphenyl group; a thienyl group; a pyridyl group; a pyridyl group substituted by one or more nitro groups; a phenylthio group; a phenyloxy group substituted by one or more halogen atoms or nitro groups; or an indolyl group, A is a group represented by:
the formula (i):

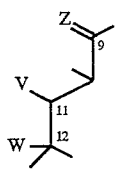

wherein Z is an oxygen atom or a group represented by the formula $=N-O-R^4$ (wherein $R^4$ is a hydrogen atom; a $C_1-C_8$ alkyl group; $-CH_2CH_2OCH_3$; $-CH_2CH_2OCH_2CH_2OCH_3$; $-CH_2CH_2OCH_2CH_2OCH_2CH_2OCH_3$; $-CH_2CH_2CH_2OCH_3$; $-CH_2CH_2SCH_3$; $-CH_2CH_2(NH)CH_2CH_2N(CH_3)_2$; $-CH_2OCH_2CH_2OCH_3$; $-CH_2CH_2N(CH_3)_2$; $-CH_2CH_2N(CH_2)(CH_2Ph)$; a benzyl group; or a benzyl group having 1 to 5 substituents selected from the group consisting of halogen atoms and $C_1-C_4$ alkyl groups), V is a hydroxyl group and W is a hydrogen atom or a hydroxyl group, or V and W represent, together with the carbon atoms at the 11- and 12-positions, a group represented by the formula:

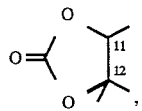

a group represented by the formula:

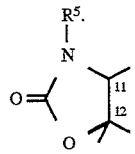

(wherein $R^5$ is a hydrogen atom or a $C_1-C_3$ alkyl group), a group represented by the formula (ii):

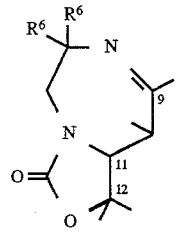

(wherein $R^6$ is a hydrogen atom or a $C_1-C_3$ alkyl group), or a group represented by the formula (iii):

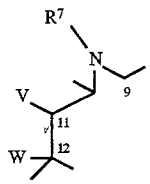

(wherein $R^7$ is a hydrogen atom, a $C_1-C_4$ alkyl group, a $C_3-C_5$ alkenyl group or $C_3-C_5$ alkynyl group, and V and W are as defined above), R' is a hydrogen atom, a $C_1-C_5$ alkyl group, a carbamoyl group or an acetyl group, R" is a hydrogen atom, a $C_2-C_{15}$ alkoxycarbonyl group, 2-[2-(2-methoxyethyoxy)ethoxy]ethoxycarbonyl group, 2-[2-(2-ethoxyethoxy)ethoxy]ethoxycarbonyl group, a $C_2-C_{15}$ acyl group, an ethylsuccinyl group, or a pyridylcarbonyl group or a pharmaceutically acceptable acid addition salt thereof.

2. A 5-0-desosaminylerythronolide derivative or a pharmaceutically acceptable acid addition salt thereof according to claim 1, wherein:

Y is a group represented by the formula:

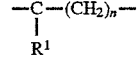

(wherein $R^1$ is a hydrogen atom, a hydroxyl group, a halogen atom or a $C_1-C_3$ alkyl group, and n is 1) or an oxygen atom, R is a phenyl group having 1 to 5 substituents selected from the group consisting of halogen atoms, nitro groups, amino groups, $C_1-C_3$ alkyl groups, $C_1-C_3$ alkyl groups substituted with one or more halogen atoms, $C_1-C_4$ alkylamino groups, $C_2-C_7$ acylamino groups and $C_1-C_4$ alkoxy groups; an aminothiazolyl group; a pyridyl group; or a phenyloxy group substituted with one or more halogen atoms or nitro groups;

A is a group represented by the formula (i) or the formula (ii),

R' is a hydrogen atom or a $C_1-C_5$ alkyl group,

R" is a hydrogen atom, 2-[2-(2-methoxyethoxy)ethoxy]ethoxycarbonyl group, 2-[2-(2-ethoxyethoxy)ethoxy]ethoxycarbonyl group, a $C_2-C_{15}$ acyl group or a pyridylcarbonyl group.

3. A 5-0-desosaminylerythronolide derivative or a pharmaceutically acceptable acid addition salt thereof according to claim 1, wherein:

Y is a group represented by the formula:

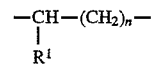

wherein $R^1$ is a hydrogen atom, a hydroxyl group, a halogen atom or a $C_1-C_3$ alkyl group, and n is 0–4, and R is a phenyl group having 1 to 5 substituents selected from the group consisting of halogen atoms, nitro groups, amino groups, $C_1-C_3$ alkyl groups substituted with one or more halogen atoms, $C_1-C_4$ alkylamino groups, $C_2-C_7$ acylamino groups and $C_1-C_4$ alkoxy groups.

4. 3-O-(4-nitrophenyl)acetyl-5-O-desosaminylerythronolide A 9-oxime 11,12-cyclic carbonate.

5. A 5-0-desosaminylerythronolide derivative or a pharmaceutically acceptable acid addition salt thereof according to claim 1, wherein:

Y is a group represented by the formula:

$$-\underset{R^1}{CH}-(CH_2)_n-$$

wherein $R^1$ is a hydrogen atom, a hydroxyl group, a halogen atom or a $C_1$–$C_3$ alkyl group, and n is 0–4, and R is a phenyl group substituted with at least one nitro group.

6. A 5-O-desosaminylerythronolide derivative or a pharmaceutically acceptable acid addition salt thereof according to claim 1, wherein:

A is (i);

Z is an oxygen atom or a group represented by the formula $=N-O-R^4$ (wherein $R^4$ is a hydrogen atom; a $C_1$–$C_8$ alkyl group; $-CH_2CH_2OCH_3$; $-CH_2CH_2OCH_2CH_2OCH_3$; $-CH_2CH_2OCH_2CH_2OCH_2CH_2OCH_3$; $-CH_2CH_2CH_2OCH_3$; $-CH_2CH_2SCH_3$; $-CH_2CH_2(NH)CH_2CH_2N(CH_3)_2$; $-CH_2OCH_2CH_2OCH_3$; $-CH_2CH_2N(CH_3)_2$; $-CH_2CH_2N(CH_3)CH_2Ph$; a benzyl group; or a benzyl group having 1 to 5 substituents selected from the group consisting of halogen atoms and $C_1$–$C_4$ alkyl groups); and V and W represent, together with the carbon atoms at the 11- and 12-positions, a group represented by the formula:

$$O=\underset{O}{\overset{O}{\bigg\langle}}\underset{12}{\overset{11}{\bigg]}}$$

7. A 5-O-desosaminylerythronolide derivative or a pharmaceutically acceptable acid addition salt thereof according to claim 5, wherein:

A is (i);

Z is an oxygen atom or a group represented by the formula $=N-O-R^4$ (wherein $R^4$ is a hydrogen atom; a $C_1$–$C_8$ alkyl group; $-CH_2CH_2OCH_3$; $-CH_2CH_2OCH_2CH_2OCH_3$; $-CH_2CH_2OCH_2CH_2OCH_2CH_2OCH_3$; $-CH_2CH_2CH_2OCH_3$; $-CH_2CH_2SCH_3$; $-CH_2CH_2(NH)CH_2CH_2N(CH_3)_2$; $-CH_2OCH_2CH_2OCH_3$; $-CH_2CH_2N(CH_3)_2$; $-CH_2CH_2N(CH_3)CH_2Ph$; a benzyl group; or a benzyl group having 1 to 5 substituents selected from the group consisting of halogen atoms and $C_1$–$C_4$ alkyl groups); and V and W represent, together with the carbon atoms at the 11- and 12-positions, a group represented by the formula:

$$O=\underset{O}{\overset{O}{\bigg\langle}}\underset{12}{\overset{11}{\bigg]}}$$

8. A 5-O-desosaminylerythronolide derivative or a pharmaceutically acceptable acid addition salt thereof according to claim 1, wherein:

A is (i);

Z is an oxygen atom or a group represented by the formula $=N-O-R^4$ (wherein $R^4$ is a hydrogen atom; a $C_1$–$C_8$ alkyl group, $-CH_2CH_2OCH_3$; $-CH_2CH_2OCH_2CH_2OCH_3$; $-CH_2CH_2OCH_2CH_2OCH_2CH_2OCH_3$; $-CH_2CH_2CH_2OCH_3$; $-CH_2CH_2SCH_3$; $-CH_2CH_2(NH)CH_2CH_2N(CH_3)_2$; $-CH_2OCH_2CH_2OCH_3$; $-CH_2CH_2N(CH_3)_2$; $-CH_2CH_2N(CH_3)CH_2Ph$; a benzyl group; or a benzyl group having 1 to 5 substituents selected from the group consisting of halogen atoms and $C_1$–$C_4$ alkyl groups); and V and W represent, together with the carbon atoms at the 11- and 12-positions, a group represented by the formula:

$$O=\underset{O}{\overset{\overset{R^5}{|}{N}}{\bigg\langle}}\underset{12}{\overset{11}{\bigg]}}$$

9. A 5-O-desosaminylerythronolide derivative or a pharmaceutically acceptable acid addition salt thereof according to claim 1, wherein A is (ii).

10. A 5-O-desosaminylerythronolide derivative or a pharmaceutically acceptable acid addition salt thereof according to claim 1, wherein A is (iii).

11. A 5-O-desosaminylerythronolide derivative or a pharmaceutically acceptable acid addition salt thereof according to claim 1, wherein Y is an oxygen atom.

12. A 5-O-desosaminylerythronolide derivative or a pharmaceutically acceptable acid addition salt thereof according to claim 1, wherein Y is a vinylene group.

13. A 5-O-desosaminylerythronolide derivative or a pharmaceutically acceptable acid addition salt thereof according to claim 1, wherein Y is $-CH_2-NH-CO-$.

* * * * *

UNITED STATES PATENT AND TRADEMARK OFFICE
CERTIFICATE OF CORRECTION

PATENT NO. : 5,631,354
DATED : May 20, 1997
INVENTOR(S) : Asaka et al

It is certified that error appears in the above-identified patent and that said Letters Patent is hereby corrected as shown below:

Col. 1, line 65, "$C_1-C_5$", both instances, should read --$C_1-C_{15}$--.

Col. 4, line 37, "(2ethoxyethoxy)" should read --(2-ethoxyethoxy)--.

Col. 5, line 52, "$R^6$ should read --$R^1$--.

Col. 22, line 46, "moles" should read --mmoles--:

Col. 29, line 27, "$cm^{-2}$" should read --$cm^{-1}$--.

Col. 35, line 18, "(SH, m, At-H)" should read --(5H, m, Ar-H)--;

Col. 36, line 63, "=30:1:01" should read -- =30:1:0.1 --.

Col. 37, line 4, "-C-NMR" should read --$^{13}$C-NMR--."

Col. 38, line 11, "moles" should read --mmoles--;

UNITED STATES PATENT AND TRADEMARK OFFICE
CERTIFICATE OF CORRECTION

PATENT NO. : 5,631,354
DATED : May 20, 1997
INVENTOR(S) : Asaka et al

It is certified that error appears in the above-indentified patent and that said Letters Patent is hereby corrected as shown below:

Col. 39, line 8, "At" should read --Ar--;

line 52, "[M/t] should read --[M/H]--.

Col. 40, line 32, "soles" should read --mmoles--.

Col. 45, line "28, "-CH$_2$CH$_2$N(CH$_2$)" should read -- -CH$_2$CH$_2$N(CH$_3$)--; and after the formula beginning at line 35, insert --or--.

Signed and Sealed this

Fourteenth Day of July, 1998

*Attest:*

*Attesting Officer*

BRUCE LEHMAN
*Commissioner of Patents and Trademarks*

UNITED STATES PATENT AND TRADEMARK OFFICE
CERTIFICATE OF CORRECTION

PATENT NO. : 5,631,354
DATED : May 20, 1997
INVENTOR(S) : Asaka et al

Page 1 of 6

It is certified that error appears in the above-identified patent and that said Letters Patent is hereby corrected as shown below:

Col. 1, line 65, "$C_1-C_5$", both instances, should read --$C_1-C_{15}$--.

Col. 2, line 14, delete "(but in the case of Y being an oxygen";

line 15, delete "atom, R is not a hydrogen atom)".

Col. 4, line 10, "$CH_2CH_2(NH)CH_2CH_2N(CH_3)_2$" should read --$CH_2CH_2NHCH_2CH_2N(CH_3)_2$--; and

UNITED STATES PATENT AND TRADEMARK OFFICE
CERTIFICATE OF CORRECTION

PATENT NO. : 5,631,354
DATED : May 20, 1997
INVENTOR(S) : Asaka et al

It is certified that error appears in the above-identified patent and that said Letters Patent is hereby corrected as shown below:

line 37, "(2ethoxyethoxy)" should read --(2-ethoxyethoxy)--.

Col. 5, line 3, "alkoxy" should read --acyl--;

the formula at line 41 which reads:

""

should read:

--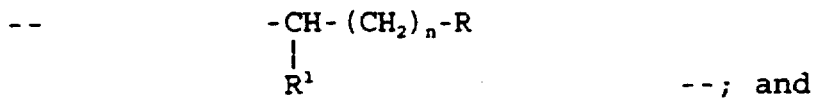--; and line 52, "$R^6$" should read --$R^8$--.

UNITED STATES PATENT AND TRADEMARK OFFICE
CERTIFICATE OF CORRECTION

PATENT NO. : 5,631,354
DATED : May 20, 1997
INVENTOR(S) : Asaka et al

It is certified that error appears in the above-identified patent and that said Letters Patent is hereby corrected as shown below:

Col. 7, line 22, "$R^2$", both instances, should read --R--.

Col. 21, line 6, "-OCOCH$_2$-" should read -- -OCOOCH$_2$- --; and line 8, "-OCOCH$_2$-" should read -- -OCOOCH$_2$- --.

Col. 22, line 46, "moles" should read --mmoles--;

line 48, delete "1.22 g of 2'-O-acetyl-";

line 49, delete entire line;

line 50, delete entire line and insert --0.93--;

line 56, "69.9" should read --169.9--.

Col. 29, line 27, "$cm^{-2}$" should read --$cm^{-1}$--.

UNITED STATES PATENT AND TRADEMARK OFFICE
CERTIFICATE OF CORRECTION

PATENT NO. : 5,631,354
DATED : May 20, 1997
INVENTOR(S) : Asaka et al

It is certified that error appears in the above-identified patent and that said Letters Patent is hereby corrected as shown below:

Col. 35, line 18, "(SH, m, At-H)" should read --(5H, m, Ar-H)--; and line 19, "(3-OCOCH$_2$-)" should read --(3-OCOOCH$_2$-)--.

Col. 36, line 63, "=30:1:01" should read -- =30:1:0.1 --.

Col. 37, line 4, "-C-NMR" should read --$^{13}$C-NMR--.

Col. 38, line 11, "moles" should read --mmoles--;

line 13, "nicotnoyl" should read --nicotinoyl--.

Col. 39, line 8, "At" should read --Ar--;

line 52, "[M/t] should read --[M/H]--.

UNITED STATES PATENT AND TRADEMARK OFFICE
CERTIFICATE OF CORRECTION

PATENT NO. : 5,631,354
DATED : May 20, 1997
INVENTOR(S) : Asaka et al

It is certified that error appears in the above-identified patent and that said Letters Patent is hereby corrected as shown below:

Col. 40, line 32, "soles" should read --mmoles--.

Col. 41, line 23, "methyamino" should read --methylamino--.

Col. 42, line 27, "121.2" should read --212.2--; and line 51, "3-O-phenylglycylglydi" should read --3-O-phenylglycylglydl--.

Col. 43, line 29, "phenylglycylglydi" should read --phenylglycylglydl--;

line 32, after "a" insert --no--; and

UNITED STATES PATENT AND TRADEMARK OFFICE
CERTIFICATE OF CORRECTION

PATENT NO. : 5,631,354
DATED : May 20, 1997
INVENTOR(S) : Asaka et al

It is certified that error appears in the above-identified patent and that said Letters Patent is hereby corrected as shown below:

line 36, "phenylglycylglydi" should read --phenylglycylglydl--.

Col. 45, line "28, "-CH$_2$CH$_2$N(CH$_2$)" should read -- -CH$_2$CH$_2$N(CH$_3$)--; and after the formula beginning at line 35, insert --or--.

This certificate supersedes Certificate of Correction issued July 14, 1998.

Signed and Sealed this

First Day of December, 1998

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,631,354
DATED : May 20, 1997
INVENTOR(S) : Asaka et al.

It is certified that error appears in the above-identified patent and that said Letters Patent is hereby corrected as shown below:

Column 1,
Line 65, "$C_1$-$C_5$", both instances, should read -- $C_1$-$C_{15}$ --.

Column 2,
Line 14, delete "(but in the case of Y being an oxygen";
Line 15, delete "atom, R is not a hydrogen atom)".

Column 4,
Line 10, "$CH_2CH_2(NH)CH_2CH_2N(CH_3)_2$" should read -- $CH_2CH_2NHCH_2CH_2N(CH_3)_2$ --; and
Line 37, "(2ethoxyethoxy)" should read -- (2-ethoxyethoxy) --.

Column 5,
Line 3, "alkoxy" should read -- acyl --;
Line 41, the formula which reads:

"    "

should read:

-- 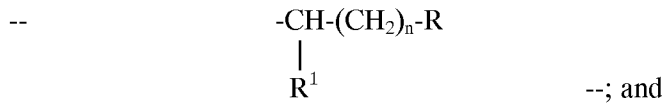 --; and

Line 52, "$R^6$ should read -- $R^8$ --.

Column 7,
Line 22, "$R^2$", both instances, should read -- R --.

Column 21,
Line 6, "-$OCOCH_2$-" should read -- -$OCOOCH_2$- --; and
Line 8, "-$OCOCH_2$-" should read -- -$OCOOCH_2$- --.

Column 22,
Line 46, "moles" should read -- mmoles --;
Line 48, delete "1.22 g of 2' -O-acetyl-";
Line 49, delete entire line;
Line 50, delete entire line and insert -- 0.93 --;
Line 56, "69.9" should read -- 169.9 --.

UNITED STATES PATENT AND TRADEMARK OFFICE
CERTIFICATE OF CORRECTION

PATENT NO. : 5,631,354
DATED : May 20, 1997
INVENTOR(S) : Asaka et al.

It is certified that error appears in the above-identified patent and that said Letters Patent is hereby corrected as shown below:

Column 29,
Line 27, "$cm^{-2}$" should read -- $cm^{-1}$ --.

Column 35,
Line 18, "(SH, m, At-H)" should read -- (5H, m, Ar-H) --; and
Line 19, "(3-OCOCH$_2$-)" should read -- (3-OCOOCH$_2$-) --.

Column 36,
Line 63, "=30:1:01" should read -- =30:1:0.1 --.

Column 37,
Line 4, "-C-NMR" should read -- $^{13}$C-NMR --.

Column 38,
Line 11, "moles" should read -- mmoles --;
Line 13, "nicotnoyl" should read -- nicotinoyl --.

Column 39,
Line 8, "At" should read -- Ar --;
Line 52, "[M/t]" should read -- [M/H] --.

Column 40,
Line 32, "soles" should read -- mmoles --.

Column 41,
Line 23, "methyamino" should read -- methylamino --.

Column 42,
Line 27, "121.2" should read -- 212.2 --; and
Line 51, "3-O-phenylglycylglydi" should read -- 3-O-phenylglycylglydl --.

Column 43,
Lines 29 and 36, "phenylglycylglydi" should read -- phenylglycylglydl --;
Line 32, after "a" insert -- no --; and

UNITED STATES PATENT AND TRADEMARK OFFICE
CERTIFICATE OF CORRECTION

PATENT NO.   : 5,631,354
DATED        : May 20, 1997
INVENTOR(S)  : Asaka et al.

It is certified that error appears in the above-identified patent and that said Letters Patent is hereby corrected as shown below:

Column 45,
Line 28, "-$CH_2CH_2N(CH_2)$" should read -- -$CH_2CH_2N(CH_3)$ --; and
Line 35, after the formula beginning, insert -- or --.

Signed and Sealed this

Twenty-fifth Day of June, 2002

Attest:

JAMES E. ROGAN
Attesting Officer       Director of the United States Patent and Trademark Office